(12) United States Patent
Zack et al.

(10) Patent No.: US 9,568,595 B2
(45) Date of Patent: Feb. 14, 2017

(54) ULTRA-WIDE BAND ANTENNA ARRAYS AND RELATED METHODS IN PERSONAL EMERGENCY RESPONSE SYSTEMS

(71) Applicant: ECHOCARE TECHNOLOGIES LTD., Beer Sheva (IL)

(72) Inventors: Rafael Zack, Kiryat Ono (IL); Ovadia Chaluba, Raanana (IL)

(73) Assignee: ECHOCARE TECHNOLOGIES LTD., Beer Sheva (IL)

( * ) Notice: Subject to any disclaimer, the term of this patent is extended or adjusted under 35 U.S.C. 154(b) by 0 days.

(21) Appl. No.: 15/008,460

(22) Filed: Jan. 28, 2016

(65) Prior Publication Data
US 2016/0377705 A1    Dec. 29, 2016

Related U.S. Application Data

(63) Continuation-in-part of application No. 14/983,632, filed on Dec. 30, 2015, which is a continuation-in-part of application No. 14/753,062, filed on Jun. 29, 2015.

(51) Int. Cl.
G08B 1/08    (2006.01)
G01S 7/41    (2006.01)
(Continued)

(52) U.S. Cl.
CPC ............ *G01S 7/414* (2013.01); *A61B 5/0826* (2013.01); *A61B 5/113* (2013.01); *A61B 5/1126* (2013.01);
(Continued)

(58) Field of Classification Search
CPC ....... A61B 5/0826; A61B 5/113; G01S 13/06; G01S 2013/0245
(Continued)

(56) References Cited

U.S. PATENT DOCUMENTS 7,567,200 B1    7/2009  Osterweil
2014/0022110 A1*  1/2014  Itohara ................... G01S 7/295
                                                          342/107
(Continued)

OTHER PUBLICATIONS

International Search Report of Application No. PCT/IL2016/050655 dated Oct. 13, 2016.

*Primary Examiner* — Tai Nguyen
(74) *Attorney, Agent, or Firm* — Pearl Cohen Zedek Latzer Baratz LLP

(57) ABSTRACT

A non-wearable Personal Emergency Response System (PERS) architecture is provided, implementing RF interferometry using synthetic aperture antenna arrays to derive ultra-wideband echo signals which are analyzed and then processed by a two-stage human state classifier and abnormal states pattern recognition. Systems and methods transmit ultra-wide band radio frequency signals at, and receive echo signals from, the environment, process the received echo signals to yield a range-bin-based slow signal that is spatio-temporally characterized over multiple spatial range bins and multiple temporal sub-frames, respectively, and derive from the slow signal multiple characteristics of human(s) in the environment. The reception antennas may be arranged in several linear baselines, implement virtual displacements, and may be set into multiple communicating sub-arrays. The decision process is carried out based on the instantaneous human state (local decision) followed by abnormal states patterns recognition (global decision).

17 Claims, 35 Drawing Sheets

(51) Int. Cl.
*G01S 13/88* (2006.01)
*G01S 13/02* (2006.01)
*A61B 5/11* (2006.01)
*A61B 5/00* (2006.01)
*A61B 5/08* (2006.01)
*A61B 5/113* (2006.01)

(52) U.S. Cl.
CPC ......... *A61B 5/7282* (2013.01); *G01S 13/0209* (2013.01); *G01S 13/886* (2013.01); *G01S 2013/0245* (2013.01)

(58) Field of Classification Search
USPC ...... 340/539.11, 539.13, 539.22; 342/21, 22, 342/28, 128, 129
See application file for complete search history.

(56) References Cited

U.S. PATENT DOCUMENTS

| | | | |
|---|---|---|---|
| 2014/0362213 A1 | 12/2014 | Tseng | |
| 2015/0124923 A1* | 5/2015 | Jeon | ........................ G06M 11/00 377/6 |

\* cited by examiner

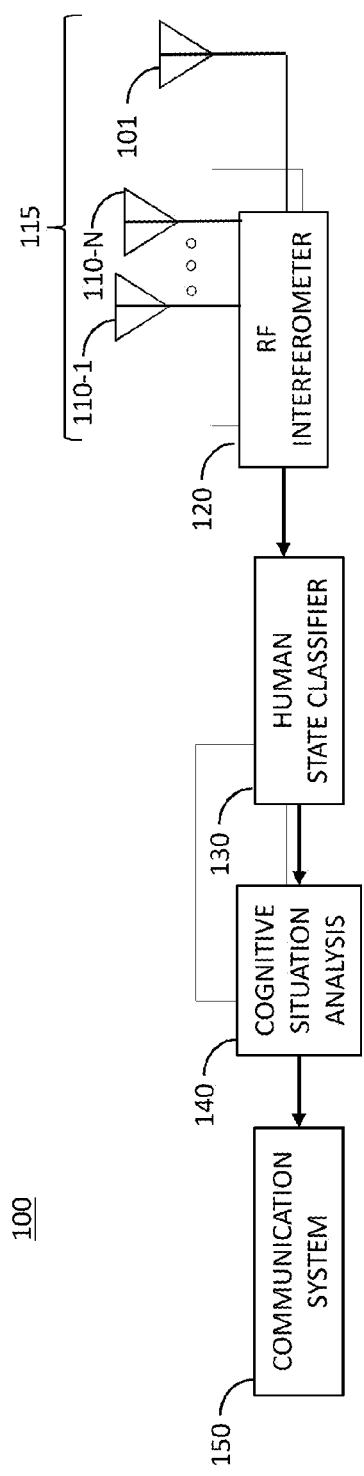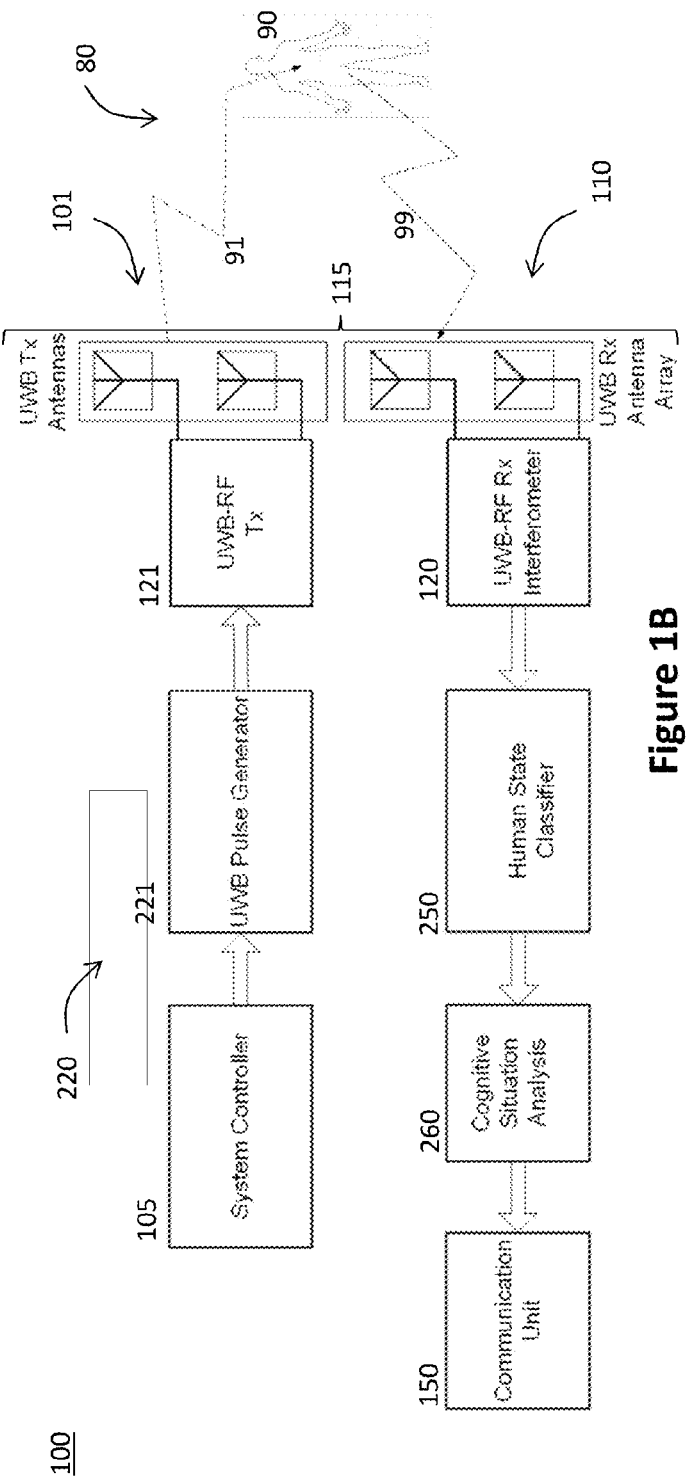

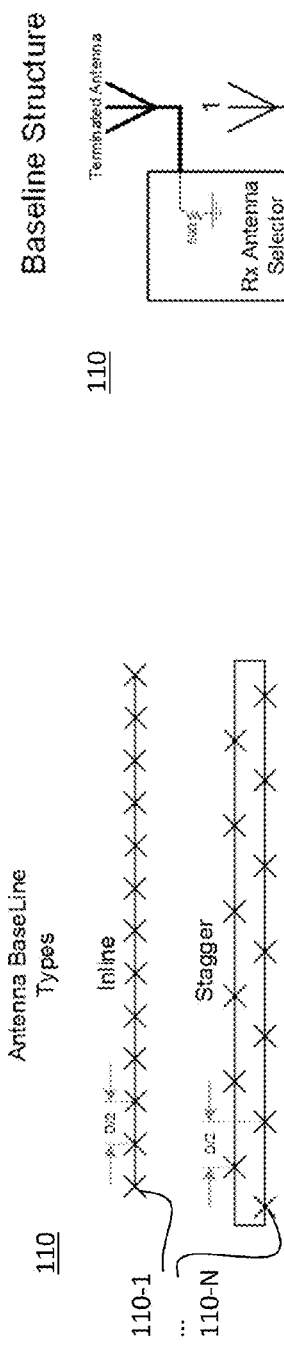
Figure 2A
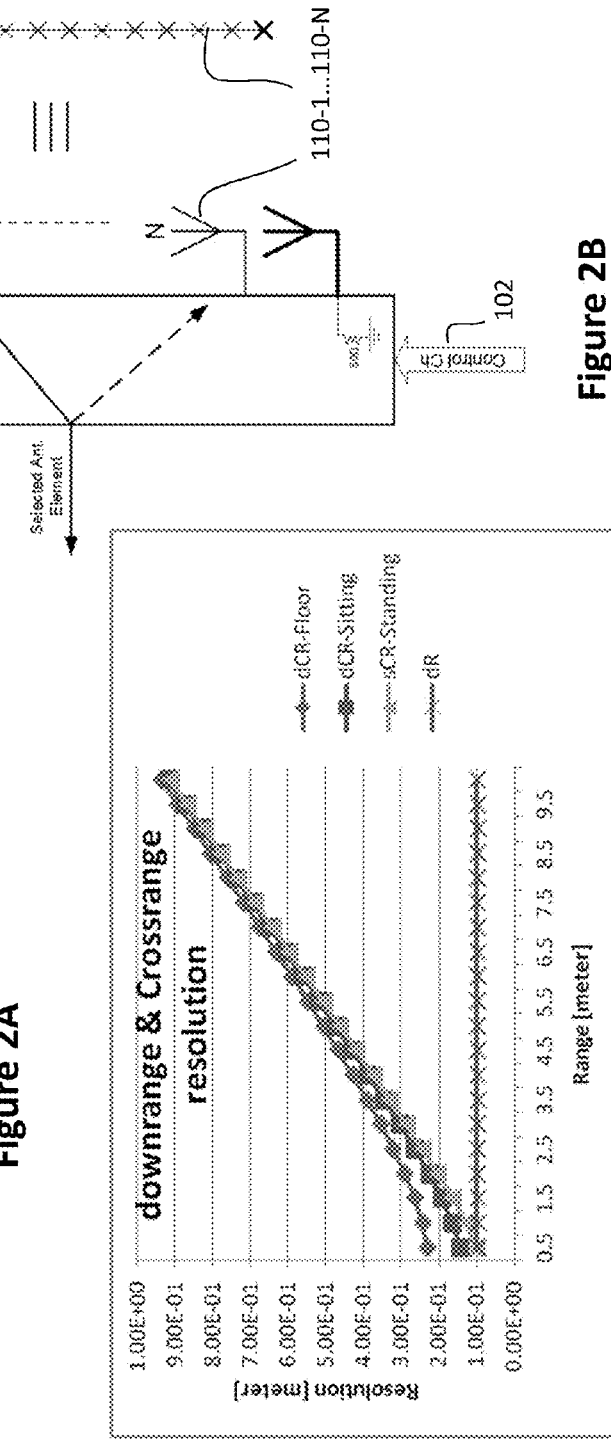
Figure 2B
Figure 2C

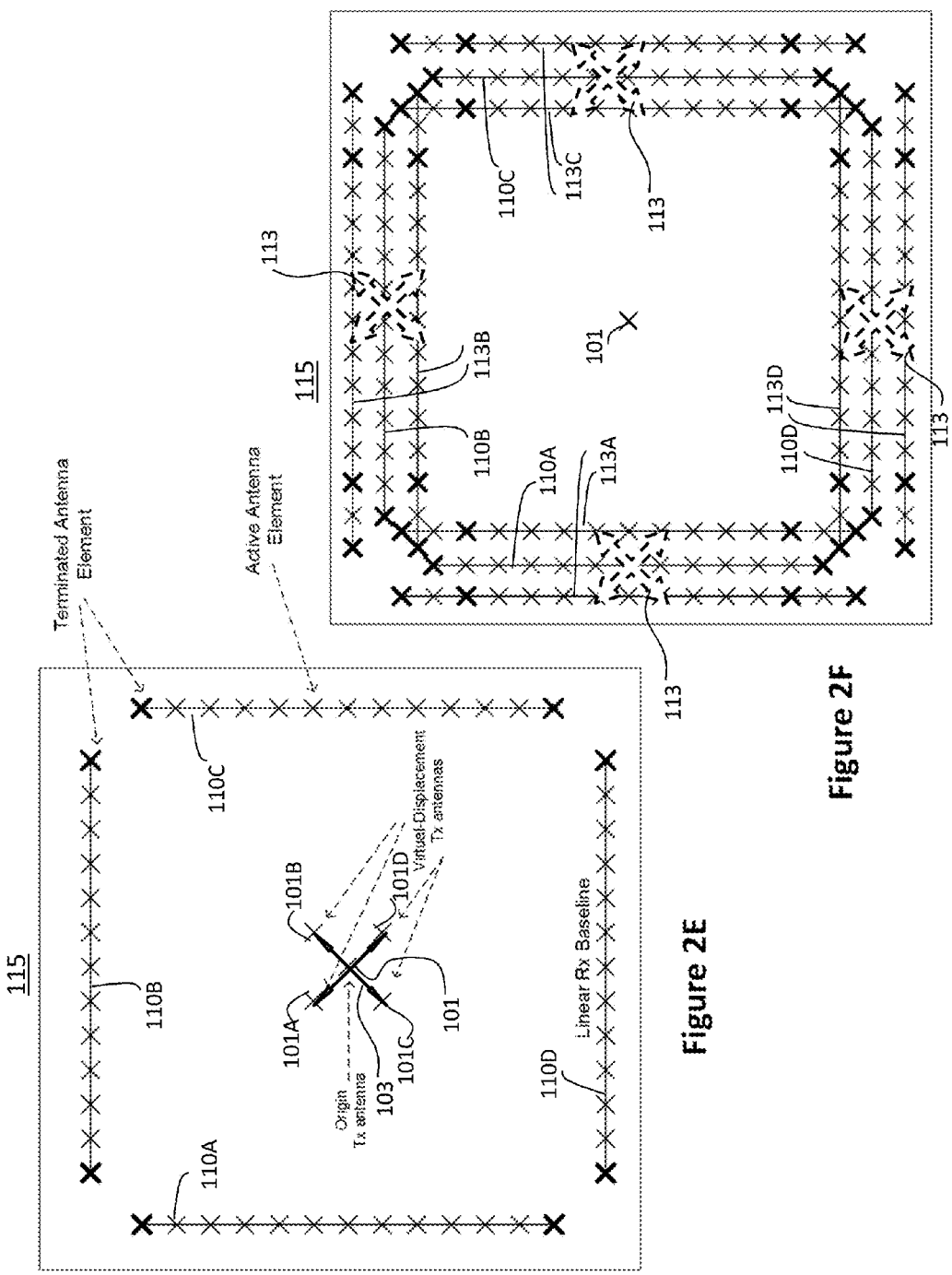

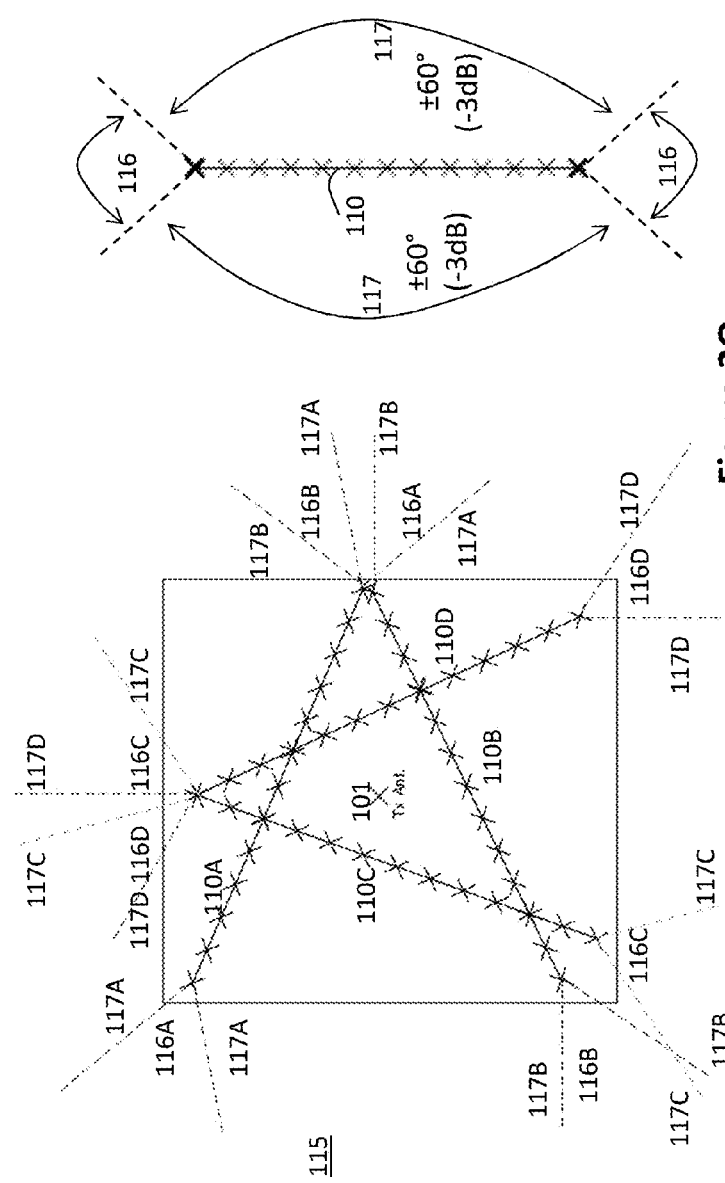
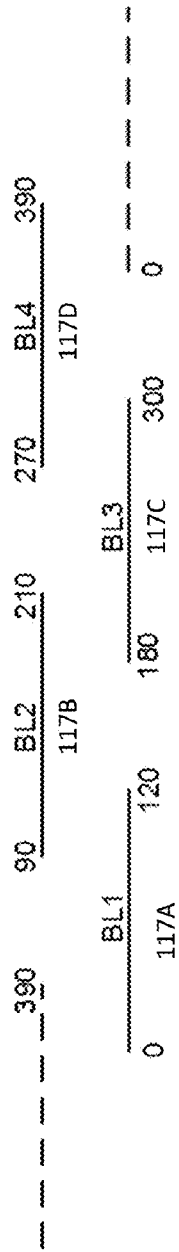
Figure 2Q
Figure 2R

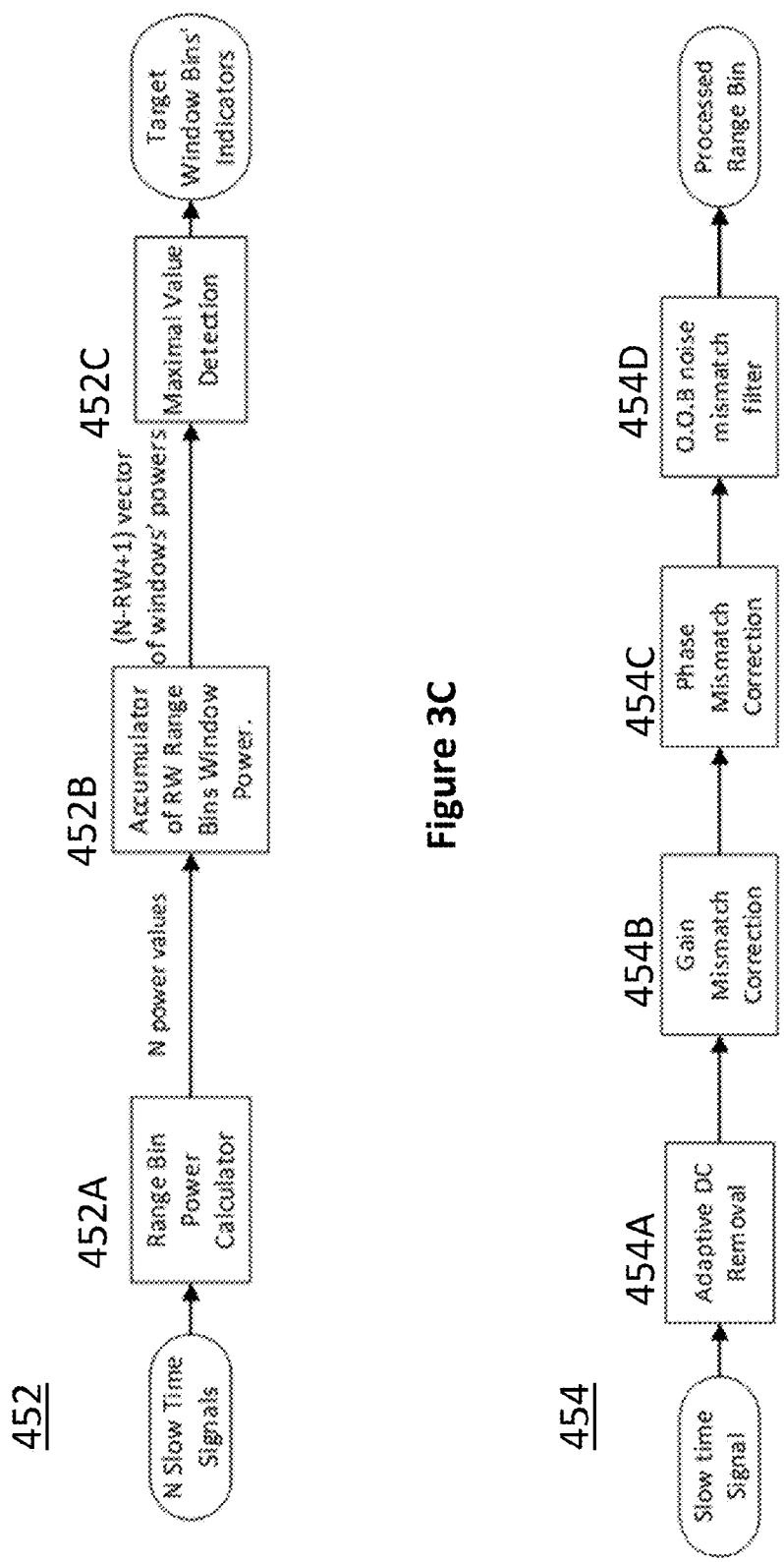

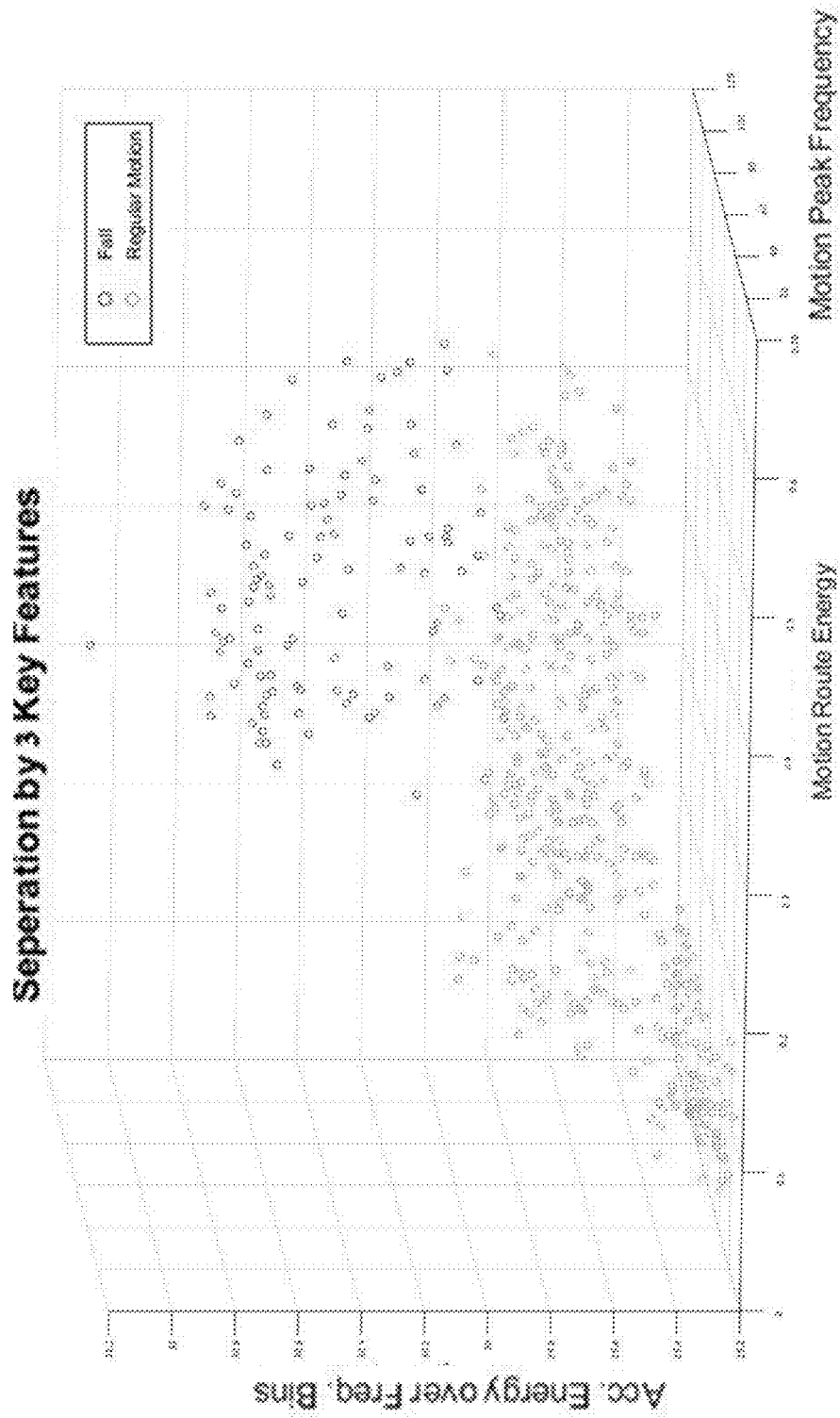
Figure 3N (Cont. 1)

VQ States Definition

| State Number | State name | Location | Human Centroid Level from Floor | Posture | Movement | Motions | Breathing (Resp/Min) | Time Limit [Minutes] |
|---|---|---|---|---|---|---|---|---|
| S1 | On floor | NA | <0.5 | Horizontal,B all | No | Minor | Normal | 5 |
| S2 | Sleeping | Bedroom | >0.5 | Horizontal | No | Minor | Normal | Daylight-180 Night-480 |
| S3 | Sleeping | Livingroom | >0.5 | Horizontal | No | Minor | Normal | Daylight-180 Night-480 |
| S4 | Sitting @ toilet | Restroom | 1 | Zigzag | No | Minor | Normal | 20 |
| S5 | Sitting | NA | 1 | Zigzag | No | Minor | Normal | 180 |
| S6 | Standing | NA | >1.5 | Vertical | No | No | Normal | 60 |
| S7 | Walking | NA | >1.5 | Vertical | Yes | Yes (Gait) | Normal | 30 |
| S8 | Falling | NA | <0.5 | NA | No | Yes | Abnormal | NA |
| S9 | Stress | NA | NA | NA | NA | Yes | Very High | 30 |
| S10 | Bath | Bathroom | >0.5/>1.5 | Zigzag/Vertical | No | Yes | Normal | 30 |

States Matrix 135

| State\Location | 1-bedroom | 2-Bathroom | 3-Restroom | 4-kitchen | 5-Livingroom | 6-other |
|---|---|---|---|---|---|---|
| 1-On floor | | | | | | |
| 2-Sleeping | X | | | | | |
| 3-Sitting | | | | | | |
| 4-Standing | | | | | | |
| 5-Walking | | | | | | |
| 6-"Falling" (Vertical motion) | | | | | | |
| 7. Stress | | | | | | |

Figure 5

CSA States Patterns

| Situation | State1 | State2 | State3 | State4 | State5 | Pattern Repetitions |
|---|---|---|---|---|---|---|
| Critical Fall 1 | S25 | S45 | S65 | S15 | S75 | 1 |
| Critical Fall 2 | S42 | S62 | S12 | S72 | X | 1 |
| Critical Fall 3 | S51 | S61 | S11 | X | X | 1 |
| Critical Fall 4 | S35 | S45 | S65 | S15 | S75 | 1 |
| High Restroom usage | S31 | S51 | S33 | S51 | S31 | >5 |
| Sedentary1 | S35 | X | X | X | X | >Time Thresh |
| Sedentary2 | S35 | S75 | X | X | X | 1 |

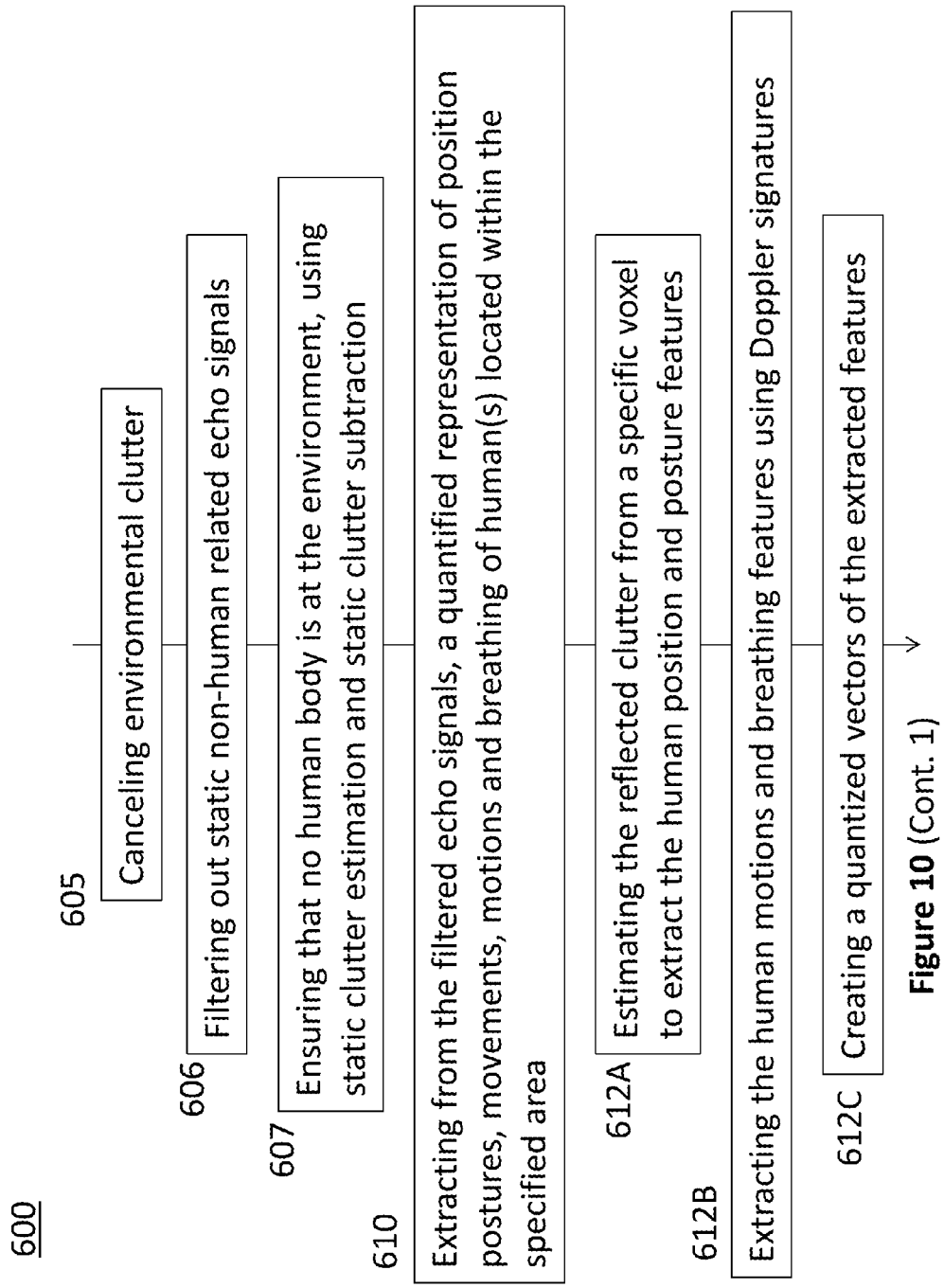
Figure 10 (Cont. 1)

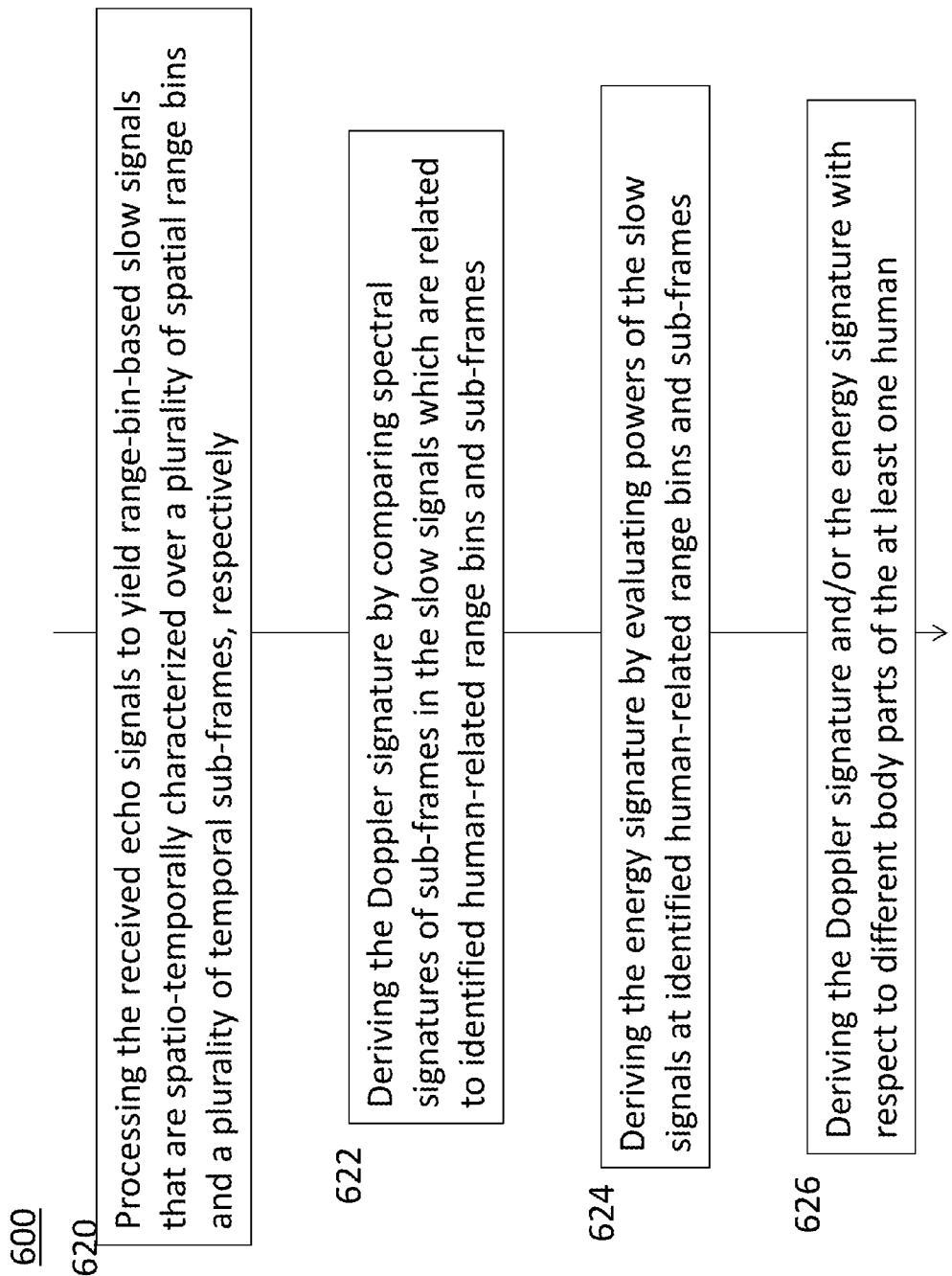
Figure 10 (Cont. 2)

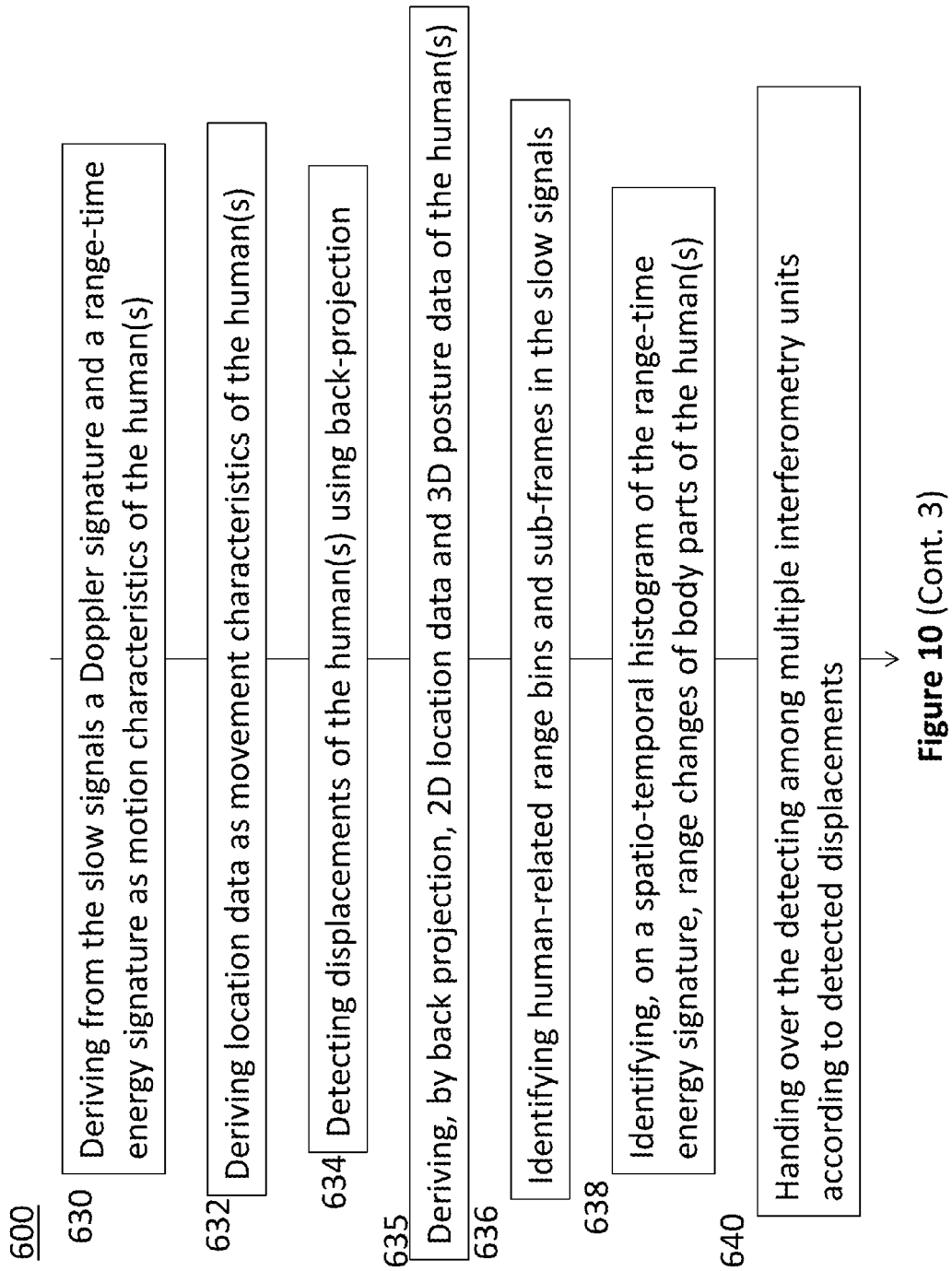
Figure 10 (Cont. 3)

600  642 — Integrating received echo signals from multiple antenna arrays and/or sub-systems 688 — Classifying any of the position, posture, motion, movement and/or respiration characteristics of the human(s) to indicate a state of the human(s)

690 — Identifying a most probable fit of human current state that represents an actual human instantaneous status 691 — Finding the best match to a codebook which represents the state being a set of human instantaneous condition/situation which is based on vector quantized extracted features 692A — Quantizing the known states features vectors and generating the states code-vectors

Figure 10 (Cont. 4)

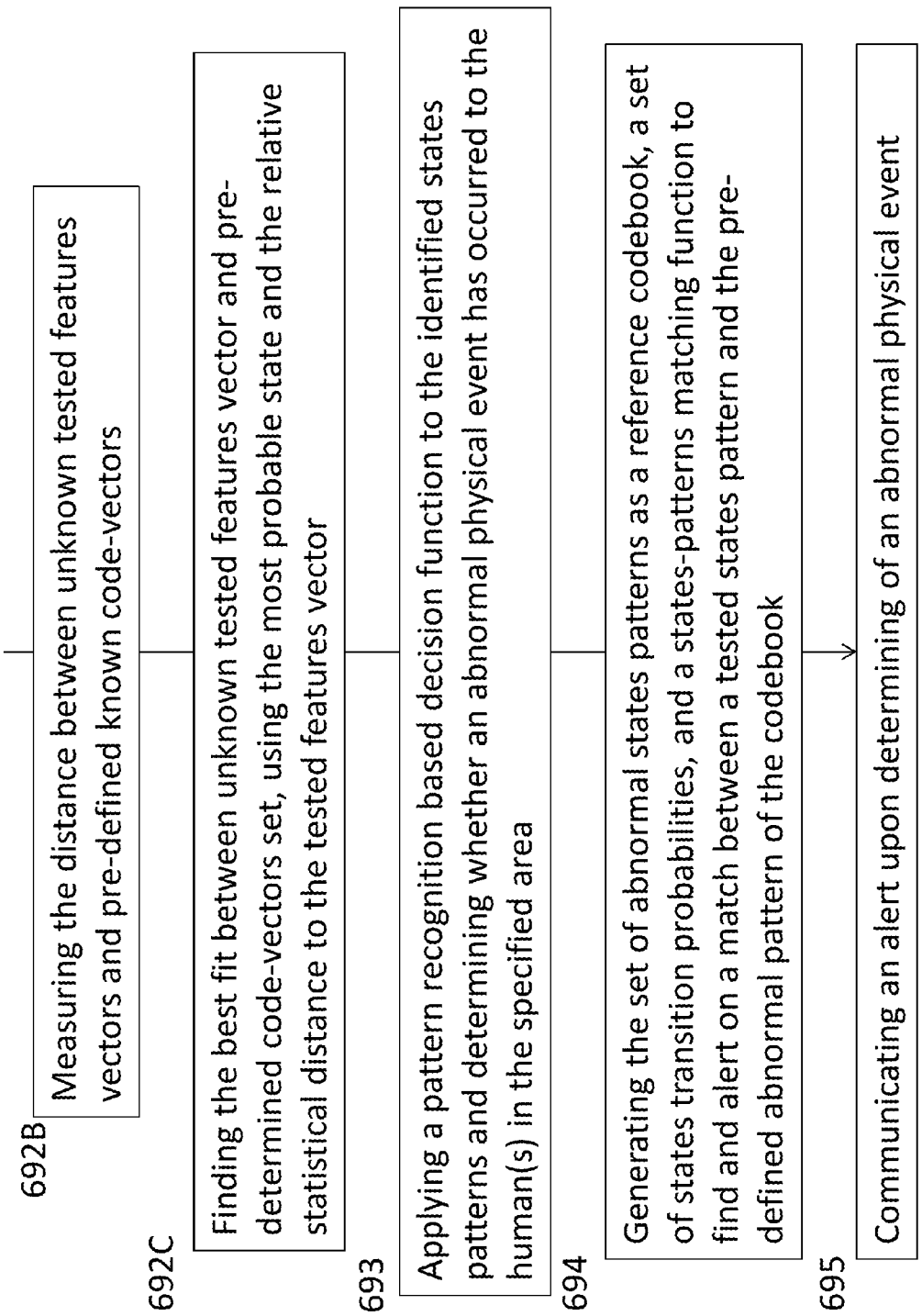
Figure 10 (Cont. 5)

ULTRA-WIDE BAND ANTENNA ARRAYS AND RELATED METHODS IN PERSONAL EMERGENCY RESPONSE SYSTEMS

CROSS REFERENCE TO RELATED APPLICATIONS

This application is a continuation-in-part of U.S. patent application Ser. No. 14/983,632, filed on Dec. 30, 2015, which in turn is a continuation-in-part of and claimed priority from U.S. patent application Ser. No. 14/753,062, filed on Jun. 29, 2015, all of which are incorporated herein by reference in their entirety.

FIELD OF THE INVENTION

The present invention relates to the field of elderly monitoring using ultra-wide band interferometry, and more particularly, to ultra-wide band antenna arrays used in personal emergency response system (PERS).

BACKGROUND OF THE INVENTION

Elderly people have a high risk of falling, for example, in residential environments. As most of elder people will need immediate help after such a fall, it is crucial that these falls are monitored and addressed in real time. Specifically, one fifth of falling elders are admitted to hospital after staying on the floor for over one hour following a fall. The late admission increases the risk of dehydration, pressure ulcers, hypothermia and pneumonia. Acute falls lead to high psychological effects of fear and negatively impact the quality of daily life.

Most of the existing personal emergency response systems (PERS), which take the form of fall detectors and alarm buttons, are wearable devices. These wearable devices have several disadvantages. First, they cannot recognize the human body positioning and posture.

Second, they suffer from limited acceptance and use due to: elders' perception and image issues, high rate of false alarms and miss-detects, elders neglect re-wearing when getting out of bed or bath, and the fact that long term usage of wearable devices might lead to user skin irritations. Third, the wearable PERS are used mainly after experiencing a fall (very limited addressable market).

Therefore, there is a need for a paradigm shift toward automated and remote monitoring systems.

SUMMARY OF THE INVENTION

Some embodiments of the present invention provide a unique sensing system and a breakthrough for the supervision of the elderly during their stay in the house, in general, and detect falls, in particular. The system may include: a UWB-RF Interferometer, Vector Quantization based Human states classifier, Cognitive situation analysis, communication unit and processing unit.

One aspect of the present invention provides a method comprising transmitting ultra-wide band (UWB) radio frequency (RF) signals at, and receiving echo signals from, an environment including at least one human, processing the received echo signals to yield a range-bin-based slow signal that is spatio-temporally characterized over a plurality of spatial range bins and a plurality of temporal sub-frames, respectively, and deriving from the slow signal a Doppler signature and a range-time energy signature as motion characteristics of the at least one human.

According to some embodiments of the present invention, the system may be installed in the house's ceiling, and covers a typical elder's apartment with a single sensor, using Ultra-Wideband RF technology. It is a machine learning based solution that learns the elder's unique characteristics (e.g., stature, gait and the like) and home primary locations (e.g. bedroom, restroom, bathroom, kitchen, entry, etc.), as well as the home external walls boundaries.

According to some embodiments of the present invention, the system may automatically detect and alert emergency situation that might be encountered by elders while being at home and identify the emergency situations.

According to some embodiments of the present invention, the system may detect falls of elderly people, but may also identify other emergencies situations, such as labored breathing, sleep apnea, as well as other abnormal cases, e.g., sedentary situation, repetitive non-acute falls that are not reported by the person. It is considered as a key element for the elderly connected smart home, and, by connecting the system to the network and cloud, it can also make use of data analytics to identify new patterns of emergencies and abnormal situations.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1A-1C are block diagrams illustrating a non-limiting exemplary architecture of a system in accordance with embodiments of the present invention.

FIGS. 2A and 2B are high level schematic illustrations of configurations of a linear baseline (SAAA), according to some embodiments of the invention.

FIG. 2C illustrates a non-limiting example for image resolution data achieved under the parameters defined above, for the various human posture and ranges from the system, according to some embodiments of the invention.

FIGS. 2E-2G are high level schematic diagrams illustrating conceptual 2D Synthetic Aperture Antennas arrays with virtual displacements, according to some embodiments of the invention.

FIGS. 2Q and 2R illustrate the coverage of the system's surroundings in the non-limiting case of four baselines, according to some embodiments of the invention.

FIG. 3C is a high-level schematic flowchart illustration of exemplary human body target detection, according to some embodiments.

FIG. 3D is a high-level schematic flowchart illustration of an exemplary slow signal preprocessing unit, according to some embodiments.

FIG. 4 is a table illustrating an exemplary states definition in accordance with some embodiments of the present invention.

FIG. 5 is a table illustrating an exemplary states matrix in accordance with some embodiments of the present invention.

FIG. 6 is a table illustrating exemplary abnormal patterns in accordance with some embodiments of the present invention.

Figure 1C:
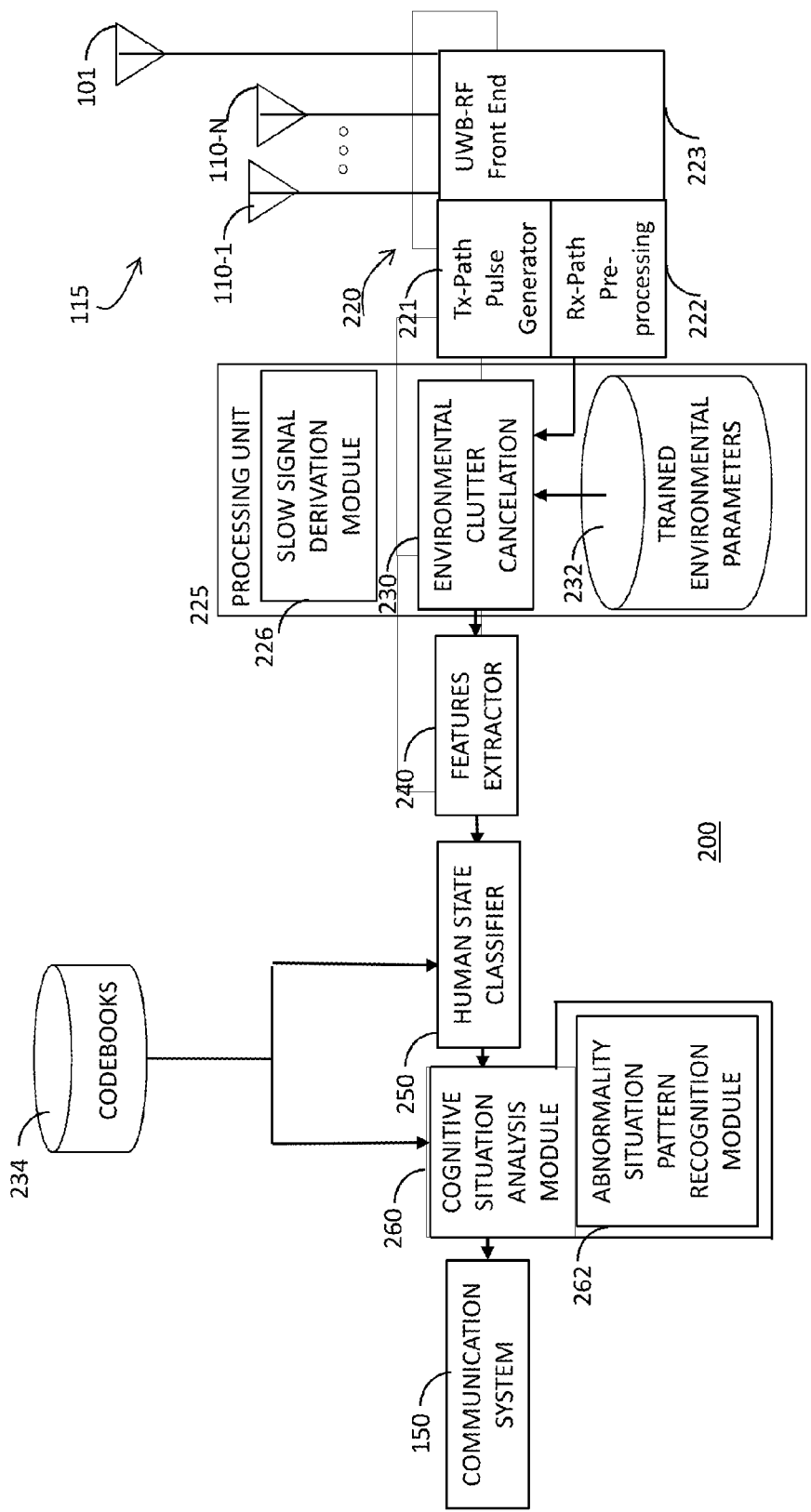

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Prior to the detailed description being set forth, it may be helpful to set forth definitions of certain terms that will be used hereinafter.

The term "slow signal" as used in this application refers to the signal derived from received echo (fast) signals and is spatio-temporally characterized over multiple range bins (as spatial units) and multiple sub-frames (as temporal units).

The term "motion" as used in this application refers to the motion of the body and/or of body parts without displacement of the whole body as a bulk, such as gestures, limb motions, posture changes such as sitting down or standing up, gait (separated from the displacement), motion suddenness (e.g., possible fall or collapse) etc.

The term "movement" as used in this application refers to the displacement of a person's body as a whole, irrespective of the motion of body parts such as the limbs. In certain embodiments, the term "movement" may be used to refer only to radial displacements and radial components of displacement with respect to the antenna, whereas tangential displacement may be discarded. In certain embodiments, tangential components of the displacement may be taken into account as movements as well.

The terms "transmission antenna" and "reception antenna" as used in this application refer are non-limiting in the sense that the system may be configured to transmit signals via antennas denoted below as reception antennas and receive echo signals via antennas denoted below as transmission antennas. It is known in the art that the terms "transmission antenna" and "reception antenna" are interchangeable in the sense that the associated electronic circuitry may be configured to reverse their respective functions. System optimization may be carried out to determine which antennas are to be operated as transmission antennas and which as reception antennas. For the sake of simplicity alone, most of the following description related to transmitting antennas as single antennas and to reception antennas as baselines (linear arrangements of antennas). It is explicitly noted that reception antennas may be single antennas and transmission antennas may be baselines, while maintaining the applicability and scope of the invention as described below.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

A sensing system is provided for the supervision and fall detection of the elderly during their stay in the house. The system combines an UWB-RF (ultra-wide band radio frequency) interferometer with a vector-quantization-based human states classifier implementing cognitive situation analysis. The UWB-RF interferometer may implement a synthetic aperture and the human states classifier may have two stages and employ abnormal states pattern recognition. The system may be installed in the house's ceiling, and cover the area of a typical elder's apartment (<100 sqm) with a single sensor, using ultra-wideband RF technology.

The system may use machine learning to learn the elder's unique characteristics (e.g., body features, stature, gait etc.) and the home environment, and uses a human state classifier to determine the instantaneous human state based on various extracted features such as human posture, motion, location at the environment as well as human respiration. The system may automatically detect, identify and alert concerning emergency situations (particularly falls) that might be encountered by elders while being at home and identifies the emergency situations. The system detects falls as well as identifies other emergency situations such as labor briefing, sedentary situations and other abnormal cases. The decision process may be done based on the instantaneous human state (local decision) followed by abnormal states patterns recognition (global decision). The system global decision (emergency alert) is communicated to the operator through the communication system and two-ways communication is enabled between the monitored person and the remote operator.

The system may comprise a communication sub-system to communicate with the remote operator and centralized system for multiple users' data analysis. A centralized system (cloud) may receive data from distributed PERS systems to perform further analysis and upgrading the systems with updated database (codebooks).

Advantageously, the system may be used as a key element for the elderly connected smart home and by connecting the system to the network and cloud, it can also make a use of big data analytics to identify new patterns of emergencies and abnormal situations. The system overcomes the disadvantages of existing PERS such as wearable fall detectors and alarm buttons, as well as visual surveillance, by recognizing the human body positioning and posture and provides a significant enhancement in acceptability as it overcomes (i) elders' perception and image issues, (ii) high rate of false alarms and misdetections, (iii) elders' neglect of re-wearing when getting out of bed or bath, and (iv) user skin irritations by long term usage of wearable devices. Moreover, it may be used to prevent the first experience of fall (after which the use of wearable devices is first considered) and does not involve privacy issues that visual surveillance system arise.

FIGS. 1A-1C are block diagrams illustrating a non-limiting exemplary architecture of a system 100 in accordance with some embodiments of the present invention. As illustrated in FIG. 1A, system 100 may include a radio frequency (RF) interferometer 120 configured to transmit signals via Tx antenna 101 and receive echo signals via array 110-1 to 110-N. Tx antennas 101 and Rx antennas 110 are part of an antenna array 115. It should be noted that transmit antennas and receive antennas may take different forms, and, according to a preferred embodiment, in each antenna array they may be a single transmit antenna and several receive antennas. An environmental clutter cancellation module may or may not be used to filter out static non-human related echo signals. System 100 may include a human state feature extractor 130 configured to extract from the filtered echo signals, a quantified representation of position postures, movements, motions and breathing of at least one human located within the specified area. A human state classifier may be configured to identify a most probable fit of human current state that represents an actual human instantaneous status. System 100 may include an abnormality situation pattern recognition module 140 configured to apply a pattern recognition based decision function to the identified states patterns and to determine whether an abnormal physical event has occurred to the at least one human in the specified area. A communication system 150 for communicating with a remote server and end-user equipment for alerting (not shown here). Communication system 150 may further include two-way communication system between the caregiver and the monitored person for real-time assistance.

As illustrated in FIG. 1B, system 100 comprises a system controller 105, a UWB-RF interferometry unit 220, a human state classifier 250, a cognitive situation analysis module 260 and communication unit 150, the operation of which is explained below (see FIG. 1C). UWB-RF interferometry unit 220 comprises a UWB pulse generator 221, a UWB RF transmission module 121, UWB transmitting antennas 101 that deliver a UWB RF signal 91 to an environment 80, e.g., one including at least one human 90, UWB receiver antennas 110 that receive echo signals 99 from the scene and UWB RF interferometer 120 that processes the received echo signals and provide signals for extraction of multiple features, as explained below. Tx antennas 101 and Rx antennas 110 are part of antenna array 115.

FIG. 1C is another block diagram illustrating the architecture of a system in further details in accordance with some embodiments of the present invention as follows. UWB-RF interferometry unit 220 transmits an ultra-wideband signal (e.g., pulse) into the monitored environment and receives back the echo signals from multiple antenna arrays to provide a better spatial resolution by using the Synthetic Antenna Aperture approach. For example, UWB-RF interferometry unit 220 may comprise transmission path pulse generator 221, UWB-RF front end 223 connected to transmitting antenna(s) 101 and reception antennas 110-1 . . . 110-N, e.g., arranged in arrays, and configured to transmit UWB RF signals generated by generator 221 to the environment and deliver echo pulses received therefrom to a reception path pro-processing module 222, possible implementing clutter cancellation with respect to clutter originating from the environment and not from human(s) in the environment. In order to increase the received signal-to-noise (SNR), the transmitter sends multiple UWB pulses and receiver receives and integrates multiple echo signals (processing gain). The multiple received signals (one signal per each Rx Antenna) are sampled and digitally stored for further signal processing.

Environmental clutter cancellation 230 may be part of a processing unit 225 as illustrated and/or may be part of UWB-RF interferometry unit 220, e.g., clutter cancellation may be at least partially carried out by a Rx path pre-processing unit 222. The echo signals are pre-processed to reduce the environmental clutter (the unwanted reflected echo components that are arrived from the home walls, furniture, etc.). The output signal mostly contains only the echo components that reflected back from the monitored human body. Environmental clutter cancellation 230 is fed with the trained environmental parameters 232. In addition, the clutter cancellation includes a stationary environment detection (i.e., no human body at zone) to retrain the reference environmental clutter for doors or furniture movement cases.

The environmental clutter cancellation is required to remove unwanted echo components that are reflected from the apartment's static items, such as walls, doors, furniture, etc. The clutter cancellation is done by subtracting the unwanted environmental clutter from the received echo signals. The residual clutter represents the reflected echo signals from the monitored human body. According to some embodiments of the present invention, the clutter cancellation also includes stationary environment detection to detect if no person is at the environment, such as when the person is not at home, or is not at the estimated zone. Therefore, a periodic stationary clutter check is carried out, and new reference clutter fingerprint is captured when the environment is identified as stationary. The system according to some embodiments of the present invention re-estimates the environmental clutter to overcome the clutter changes due to doors or furniture movements.

Feature extractor 240 that processes the "cleaned" echo signals to extract the set of features that will be used to classify the instantaneous state of the monitored human person (e.g. posture, location, motion, movement, breathing, see more details below). The set of the extracted features constructs the feature vector that is the input for the classifier.

Human state classifier 250—The features vector is entered to a Vector Quantization based classifier that classifies the instantaneous features vector by statistically finding the closest pre-trained state out of a set of N possible states, i.e., finding the closest code vector (centroid) out of all code vectors in a codebook 234. The classifier output is the most probable states with its relative probability (local decision).

Cognitive Situation Analysis (CSA) module 260—This unit recognizes whether the monitored person is in an emergency or abnormal situation. This unit is based on a pattern recognition engine (e.g., Hidden Markov Model—HMM, based). The instantaneous states with their probabilities are streamed in and the CSA search for states patterns that are tagged as emergency or abnormal patterns, such as a fall. These predefined patterns are stored in a patterns codebook 234. In case that CSA recognizes such a pattern, it will send an alarm notification to the healthcare center or family care giver through the communication unit (e.g., Wi-Fi or cellular). Two-way voice/video communication unit 150—this unit may be activated by the remote caregiver to communicate with the monitored person when necessary. UWB-RF interferometry unit 220 may include the following blocks: (i) Two-Dimensional UWB antenna array 110-1-110-N to generate the synthetic aperture through all directions, followed by antenna selector. (ii) UWB pulse generator and Tx RF chain to transmit the pulse to the monitored environment UWB Rx chain to receive the echo signals from the antenna array followed by analog to digital converter (ADC). The sampled signals (from each antenna) are stored in the memory, such as SRAM or DRAM.

In order to increase the received SNR, the RF interferometer may repeat the pulse transmission and echo signal reception per each antenna (of the antenna array) and coherently integrate the digital signal to improve the SNR.

Antenna Array and Interferometer

In order to successfully classify the human posture (based on the received echo signals) from any home location, an optimized 2-Dimensional (2D) switched antenna array with a very wide field of view (FOV) was designed to generate the 3-dimensional (3D) back-projection image with a small, or even with a minimal number of antennas. In order to cover the complete home environment, it may be split into several home cells, each with an installed system that detects and tracks the monitored person through the home environment. Coverage and infrastructure consideration may be used to determine the exact system configuration at different home environment. When the monitored person moves from one home cell to another, a pre-defined set of criteria may be used to determine whether to hand-over the human tracking from one cell to another. The width of the antenna array FOV may be configured to reduce the number of home cells while maintain the system's efficiency and reliability.

Figure 2D:
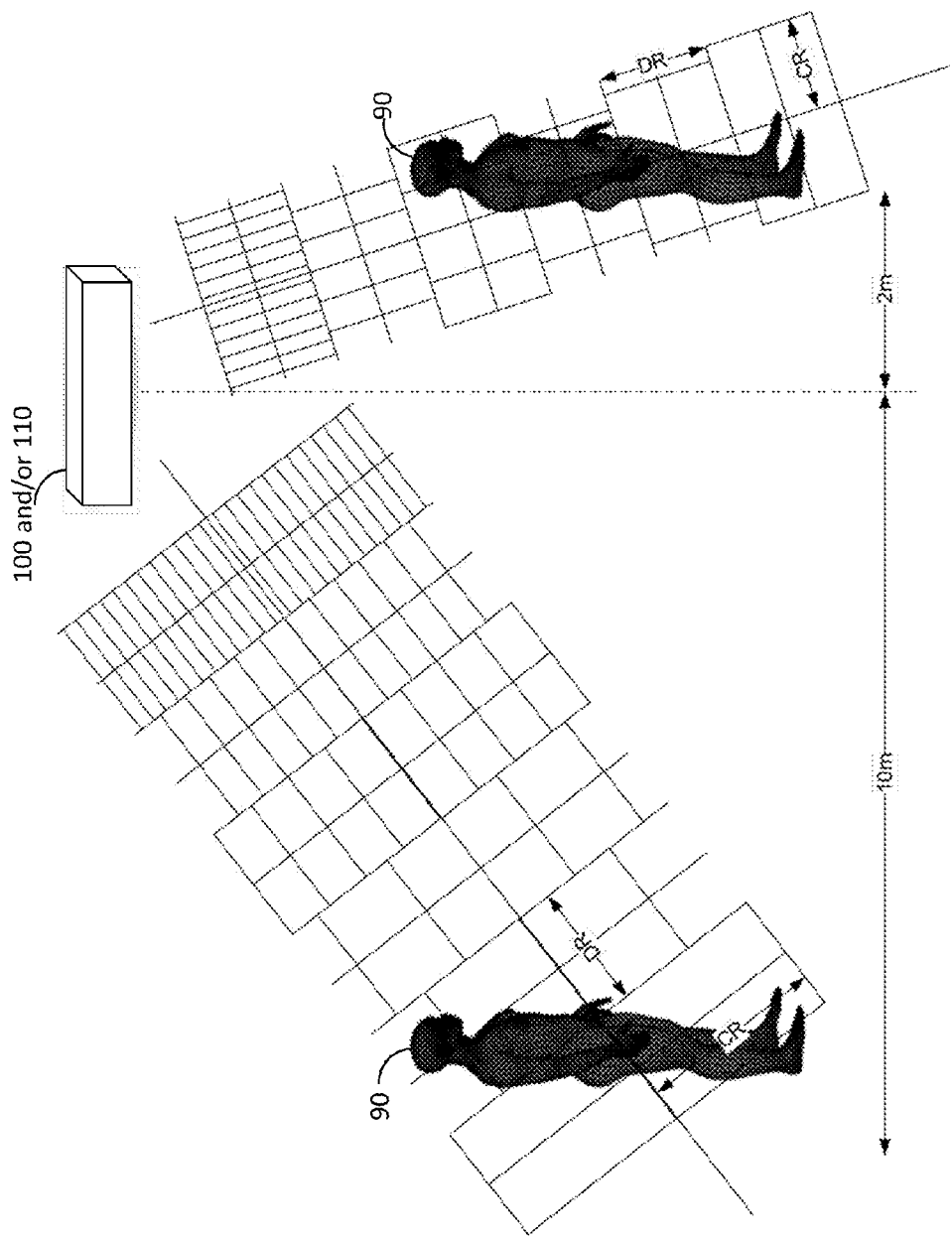
FIG. 2D schematically illustrates the dependency of image resolution on the orientation of the object, according to some embodiments of the invention.

FIGS. 2A and 2B are high level schematic illustrations of configurations of a linear baseline (SAAA) 110, according to some embodiments of the invention. FIG. 2A schematically illustrates an inline configuration with individual elements separated by D/2 and a staggered configuration with two lines of alternating elements separated by D/2 (on each line elements are separated by D). FIG. 2B schematically illustrates some more details of linear baseline 110. FIG. 2C illustrates a non-limiting example for image resolution data achieved under the parameters defined above, for the various human posture and ranges from system 100, according to some embodiments of the invention. FIG. 2D schematically illustrates the dependency of image resolution on the orientation of the object, according to some embodiments of the invention.

The human posture may be determined by analyzing and classifying the 3-dimentional human image as reconstructed by the back-projection function based on the received echo signals (see above). The image resolution is determined by the interferometer's Down Range (the image resolution in the interferometer's radial direction—$\Delta R_{dr}$) and Cross Range (the image resolution in the interferometer's angular direction—$\Delta R_{cr}$), with $\Delta R_{dr}$ determined by the transmitted pulse width and $\Delta R_{cr}$ determined by the Antenna Aperture and the range from the interferometer. In order to increase the antenna aperture, a Synthetic Aperture Antenna Array (SAAA) approach may be used by a switched antenna array. Every SAAA is termed herein a Baseline.

The resolutions for SAAA (Baseline) 110 is given by $\Delta R_{dr}=c/2B.W.$ and $\Delta R_{cr}=\lambda R/S.A.$ with c being the speed of light, B.W. being the pulse bandwidth, $\lambda$ being the wave length, R being the range from the system's antenna 110, and S.A. being the synthetic aperture. $\Delta R_{dr}$ and $\Delta R_{cr}$ are selected to ensure that classifier 250 can recognize the human posture. As a non-limiting example, the following parameter ranges may be used: B.W. between 1 and 3 GHz (in a non-limiting example, B.W.=1.5 GHz), $\lambda$ between 0.03 m and 0.1 m (in a non-limiting example, $\lambda$=0.06 m), f between 3 and 9 GHz (in a non-limiting example, f=5 GHz), S.A.

between 0.1 m and 0.7 m (in a non-limiting example, S.A.=0.33 m), $N_{antennas}$ between 3 and 21 antennas per baseline (in a non-limiting example, N=12), Antenna spacing between 0.03 m and 0.1 m (in a non-limiting example, 0.03 m) with respect to scene parameters: Ceiling height=2.5 m, sitting person height=1 m, standing person height=1.5 m. Terminated antennas are shown as elements that regulate the operation of the last receiver antennas 110-1 and 110-N in the row.

FIG. 2C presents image downrange and cross-range resolutions with respect to the floor (assuming system 100 is mounted on the ceiling) to a sitting person, a standing person and laying person on floor. The linear baseline may be considered as a switched antenna array in a constant spacing between each antenna element 110-1 . . . 110-N. Specific antenna elements may be selected through a control channel 102 to perform the synthetic aperture.

FIG. 2D schematically illustrates the dependency of image resolution on the orientation of the object, according to some embodiments of the invention. The resolution is illustrated schematically by the size of the rectangles in the figure. As seen in FIG. 2C, the DownRange (DR) resolution is constant (depends on the bandwidth) while the Cross-Range (CR) resolution depends on the antenna aperture and on the distance of the human from antenna array 110 of system 100.

Figure 2G:
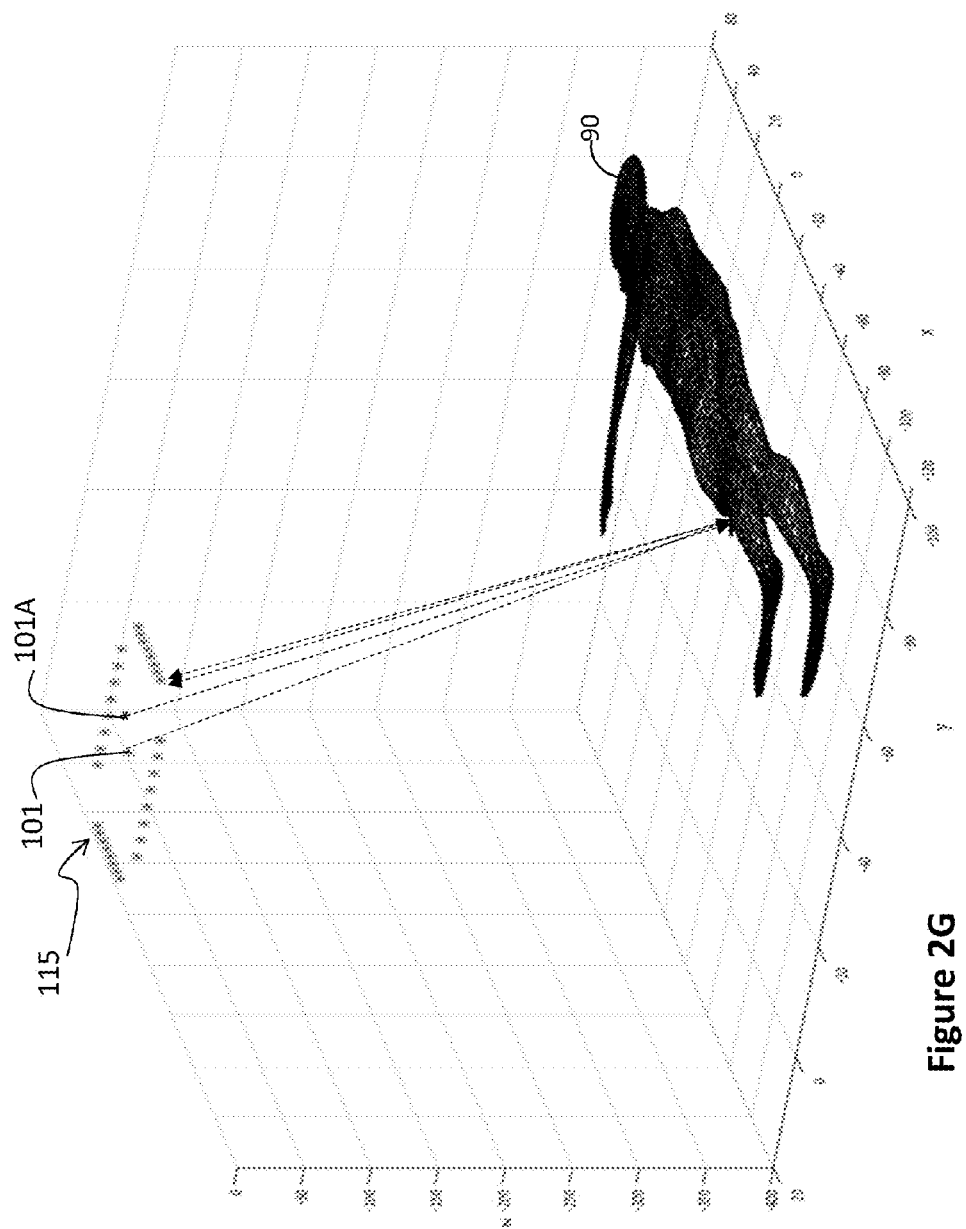

FIGS. 2E-2G are high level schematic diagrams illustrating conceptual 2D Synthetic Aperture Antennas arrays 115 with virtual displacements, according to some embodiments of the invention. In FIG. 2E, antenna array system 115 may include several linear arrays of antennas 110A, 110B, 110C and 110D, as a non-limiting example Each row (linear antenna 110A-D) may have a plurality of receive antennas 110-1 . . . 110-N as explained above; and/or additional transmission and/or reception antennas may be part of array 115. As a non-limiting example, one or more Tx antennas 101, 101A-D are illustrated at the central region of array 115. The solid line arrowed X marked 103 in FIG. 2E illustrates the relative shifts of Tx antennas 101A-D with respect to Tx antenna 101.

In FIG. 2F, 2D array structure 115 is shown with four baselines (linear arrays) 110A-D located along sides of a square. Tx antenna(s) 101 may be at the central region of 2D array structure 115. FIG. 2F illustrates schematically the effect of using virtual-displacement Tx Antennas 101A-D as virtual movements of Rx baselines 110A-D in a same displacement vector (step and direction) as the moves from the respective virtual-displacement Tx Antenna 101A-D to the original central Tx Antenna 101. The virtual displacements marked are denoted by broken line arrowed X's marked 113. Virtual displacement of Tx antenna 101 to 101A-D, e.g., by toggling between original central Tx antenna 101 and any of virtual-displacement Tx Antennas 101A-D introduces additional set of echo signals (Scatter) with different Radar Cross Section (RCS) from the target person with different signals' phases as a result of new roundtrip path from transmitting antenna, target, and reception baselines (antennas arrays). The additional diverse scatter (four additional echo signals sets) improves the reconstructed image in both additional processing gain (target reflection intensity) as well as additional information due to the Tx antenna diversity.

It is emphasized that the indication of the transmission antenna(s) as antenna elements 101 (and/or 101A-D) and the indication of the reception baseline(s) as antenna elements 110 (e.g., 110A-D) may be reversed, i.e., antenna elements 101 (and/or 101A-D) may be used as reception antennas and antenna elements 110 (e.g., 110A-D) may be used as transmission antennas. System 100 may be configured with reception antennas 101 and transmission antennas 110.

In FIG. 2G, 2D array structure 115 is shown with four linear arrays 110A-D located along sides of a square and Tx antenna 101 at the center of the square. Baseline arrays 110A-D may be virtually displaced (marked schematically by the gray arrowed X's) to yield additional virtual baselines 113A-D to improve the back-projection image (see above) by increasing the number of echo signals 99 with additional diversity. Virtual displacements of baseline arrays 110A-110D (FIG. 2G) may be combined with virtual displacements of Tx antenna 101 (FIG. 2F) as well as with non-square positions (FIG. 2E) in any practical configuration to optimize the antenna array configuration with respect to performance, size and cost.

UWB RF interferometer 120 may be to use multiple antennas to implement virtual displacement of the baselines—either multiple antennas 101 are reception antennas and the virtual displaced baselines 110 are transmitting baselines, or multiple antennas 101 are transmitting antennas and the virtual displaced baselines 110 are reception baselines.

Figure 2H:
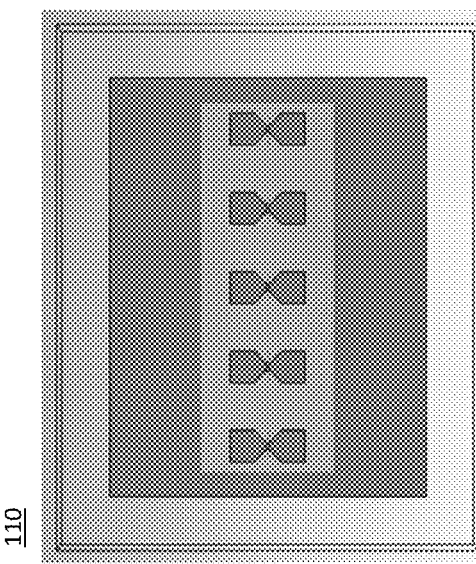
FIGS. 2H-2J are high level schematic illustrations of linear antennas arrays, according to some embodiments of the invention.
Figure 2I:
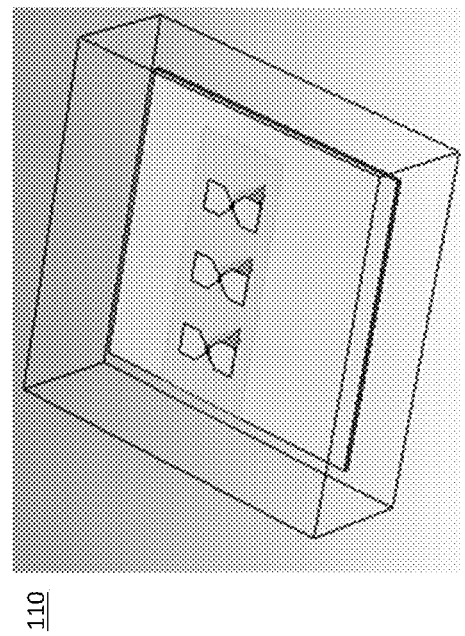
Figure 2J:
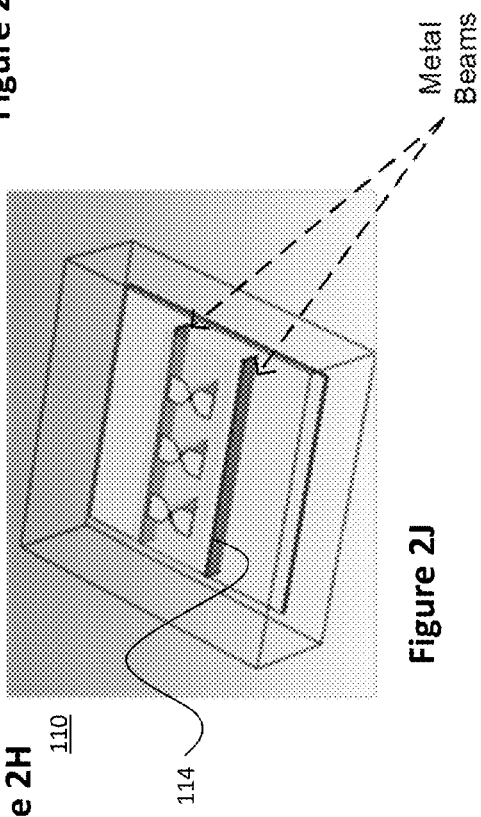
Figure 2K:
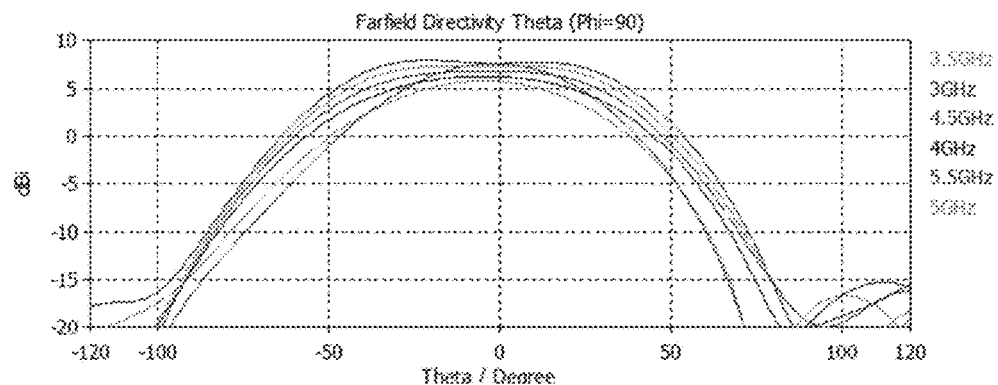
FIGS. 2K and 2L are simulation results that present the field of view of the array designs, according to some embodiments of the invention.
Figure 2L:
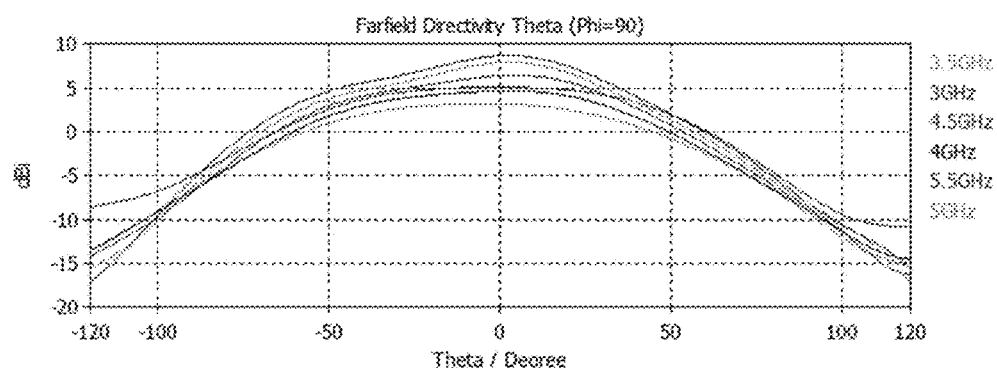
Figure 2M:
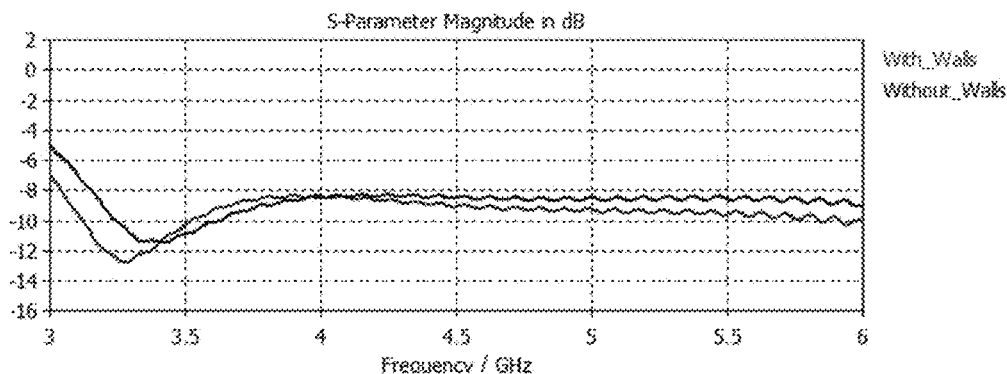
FIG. 2M shows simulation results that present the VSWR (Voltage Standing Wave Ratio) with and without metal beams, or walls, according to some embodiments of the invention.

FIGS. 2H-2J are high level schematic illustrations of linear antennas arrays 115, according to some embodiments of the invention. FIGS. 2K and 2L are simulation results that present the FOV of the array designs, according to some embodiments of the invention. The simulations are electromagnetic simulations at the E-Plane. As shown above, the major requirement from the linear antenna array for home environment is having a large field of view, which becomes a real challenge for a UWB antenna array. An innovated approach of widening the antenna array field of view is presented herein. Exemplary implementations of UWB antenna element 110 illustrated in FIGS. 2H-2J provide Field Of View (FoV) performances that are described in FIG. 2K (for the configuration of FIGS. 2H, 2I) and FIG. 2L (for the configuration of FIG. 2J) for a range of UWB frequencies. FIG. 2J schematically illustrates the addition of (e.g., two) metal beams 114 added along array 110 that widen the FOV, as illustrated in the simulation results in FIG. 2L (compare the wider FOV with respect to FIG. 2K). FIG. 2M shows simulation results that present the VSWR (Voltage Standing Wave Ratio) with and without metal beams 114 (=walls), according to some embodiments of the invention. FIG. 2M illustrates that metal walls 114 improve the antenna's VSWR at the relevant operation UWB band (4-6 GHz) with respect to an antenna lacking walls 114.

In certain embodiments, a BALUN (Balance/Unbalance unit) may be located vertically below the antennas strip (e.g., one or more of baselines 110).

Figure 2O:
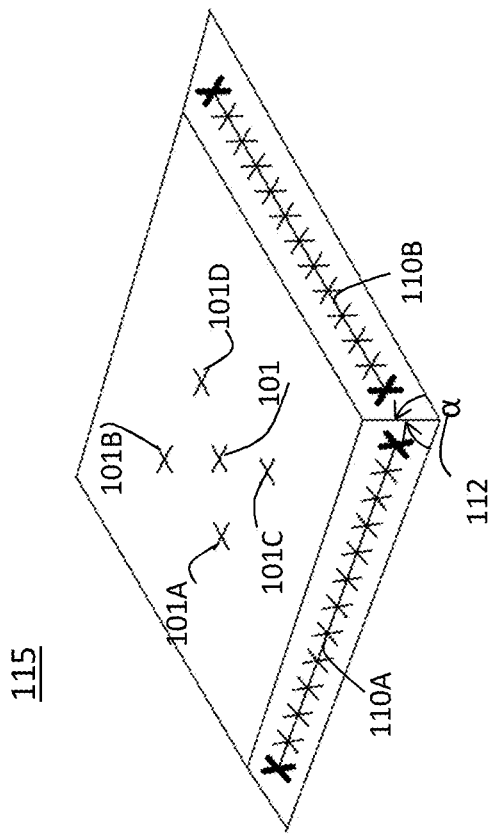
FIGS. 2N and 2O schematically illustrate an antenna array with tilted baselines, according to some embodiments of the invention.
Figure 2N:
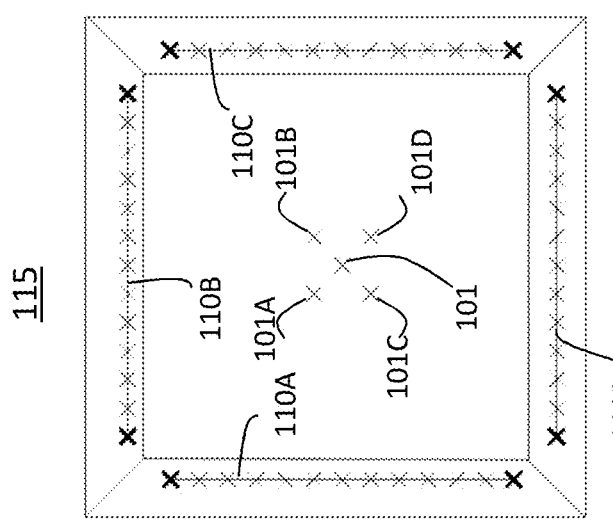

FIGS. 2N and 2O schematically illustrate antenna array 115 with tilted baselines 110A-D, according to some embodiments of the invention. Baselines 110A-D may be tilted from their common plane, e.g., by a tilt angle α 112 ranging e.g., between 10-60°, so that, when antenna array 115 is installed on a ceiling, baselines 110A-D do not face directly downwards but somewhat sideways, by tilt angle α 112. The provided tilt provides a larger field of view of antenna array 115 and hence system 100. An optimization may be carried out involving as parameters e.g., the antenna array unit vertical dimension (enabling the tilt), the field of view of the baselines and the array, and the degree of overlap between different baselines.

Figure 2P:
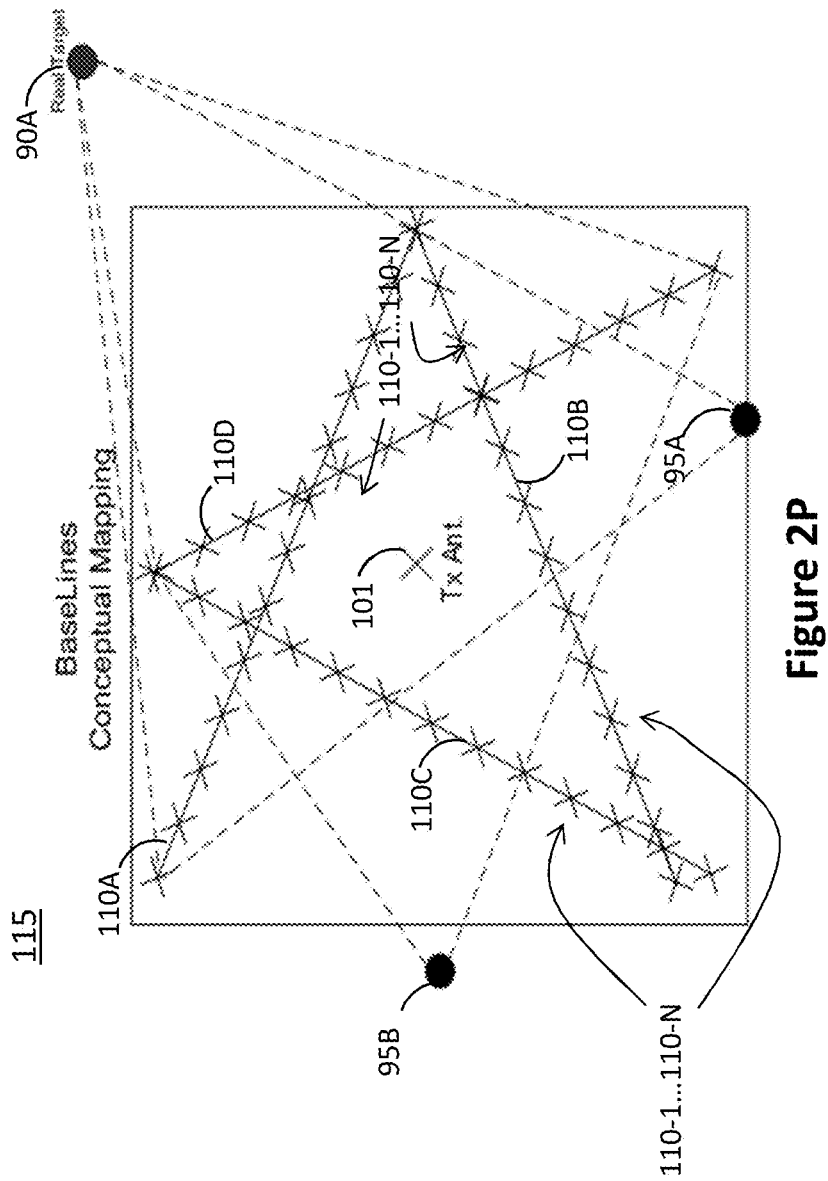
FIG. 2P is high level schematic illustrations of conceptual 2D Synthetic Aperture Antennas arrays providing unambiguous positioning, according to some embodiments of the invention.

FIG. 2P is a high level schematic illustrations of conceptual 2D Synthetic Aperture Antennas arrays 115 providing unambiguous positioning, according to some embodiments of the invention. These embodiments of non-limiting exemplary configurations enable to validate a location of a real target 90A by eliminating the possible images 95A and 95B after checking reflections 99 received at corresponding sub-arrays of antennas 110A and 110D, respectively. It is well understood that these configurations are non-limiting examples and other antennas configurations may be used effectively. Any combinations of embodiments of antenna arrays 115 illustrated herein are also considered part of the present invention. Two-dimensional array 115 guarantees that echo signals 99 are received from any direction around array 115 (assuming that each baseline 110A-D has a field of you of at least 120 degrees), and as shown in the illustration, solves the direction ambiguity of each individual baseline.

FIGS. 2Q and 2R illustrate the coverage of the system's surroundings in the non-limiting case of four baselines 110A-D, according to some embodiments of the invention. In FIG. 2Q, the coverage 117A-D of each baseline 110A-D is illustrated alongside uncovered angular ranges 116A-D. For the sake of clarity, single baseline 110 with coverage angular ranges 117 and uncovered angular ranges 116 is also illustrated. In this schematic non-limiting illustration, coverage angular ranges 117 are considered as being within the primary beam of the baseline (−3 dB), between +60° and −60°. It is noted that wider or narrower definitions may be alternatively used with respect to the baseline and system performance and requirements.

FIG. 2R exemplify possible angular ranges 117A-D in degrees (relating to 360° as the full circle coverage around array 115, i.e., 390°=30°) which cover the whole range around array 115 with overlaps in baseline ranges covered by two baselines. The FoV is defined as the −3 dB points and may be designed to cover 120° (±60°). Baselines 110 may be arranged to cover 360° with respect to array 115 with a certain overlap between baselines 110. Complementarily, baselines 110 may be arranged to solve the human target direction ambiguity by sufficient coverage and overlap requirements. Similar consideration may be taken with respect to either or both primary and secondary beams.

Figure 2S:
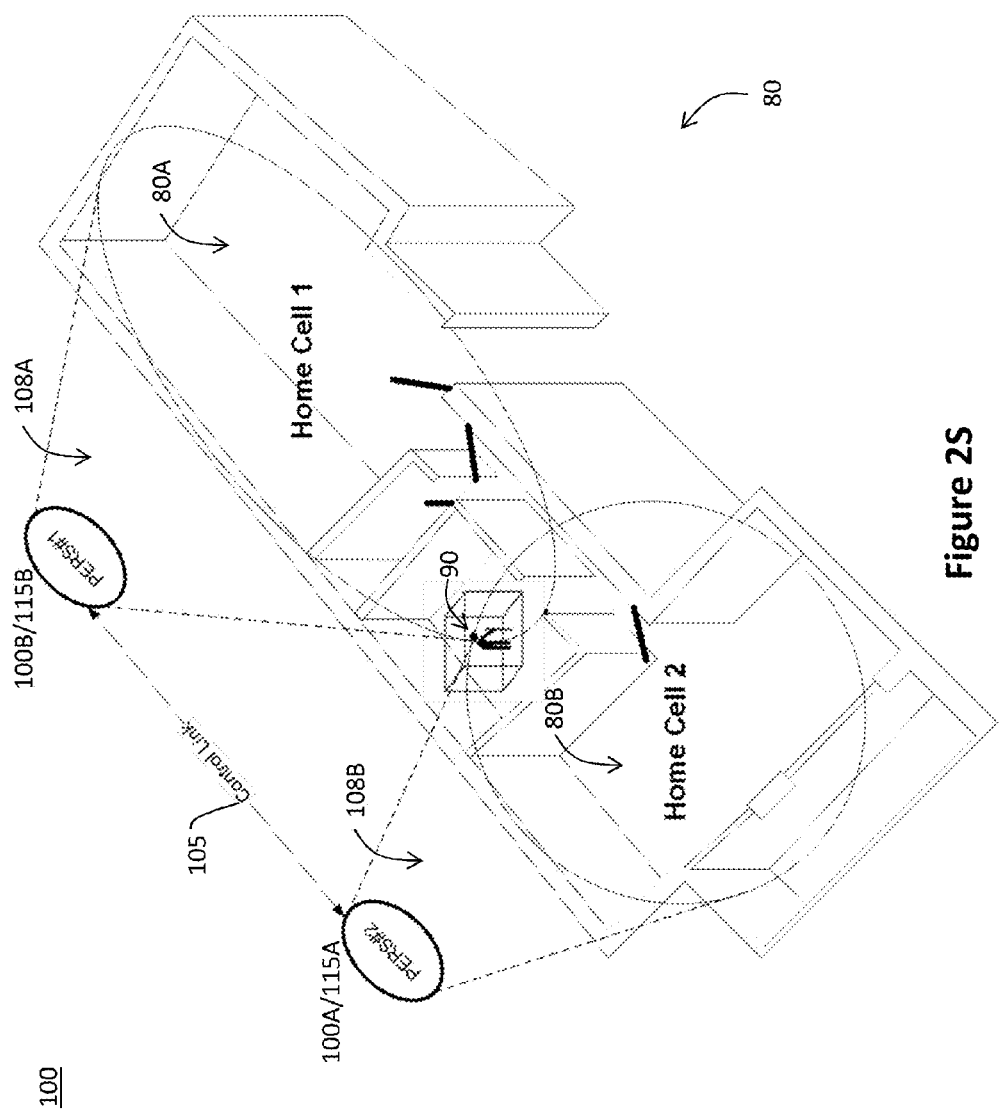
FIG. 2S is a high level schematic illustration of the system with two home cells as a non-limiting example, according to some embodiments of the invention.

FIG. 2S is a high level schematic illustration of system 100 with two home cells 108A and 108B as a non-limiting example, according to some embodiments of the invention. In some houses/apartments environments 80, PERS system 100 may comprise more than one sub-systems 100A, 100B and/or more than one antenna arrays 115A, 115B to cover whole environment 80 effectively and to monitor target person 90 everywhere in environment 80. For example, home environment 80 may be split into several home cells 80A, 80B, with respective sub-systems 100A, 100B and/or antenna arrays 115A, 115B that create respective sub-cells 108A, 108B. Sub-systems 100A, 100B, etc. may each comprise, e.g., a UWB RF interferometry unit, a human state feature extractor and a human state classifier. Control unit 105 of system 100 regulates (e.g., according to a pre-defined set of criteria) hand-overs between sub-systems 100A, 100B and/or between antenna arrays 115A, 115B as monitored person 90 moves between home cells 108A, 108B, while maintaining continuous detection and tracking. Examples for handing over criteria comprise: (i) $BPI_i > BPI_j$ with BPI being the back-projection (accumulated) intensity from the monitored person as received at $PERS_i$ 100A and $PERS_j$ 100B; and/or (ii) $PDR_i < PDR_j$ with PDR being the person down range distance from PERSi 100A and PERSj 100B as is estimated by each PERS unit. Abnormality situation pattern recognition module 140 of system 100 may be further configured to integrate input from all sub-systems 100A, 100B etc.

The multiple PERS sub-systems may hand-over person tracking among themselves by any of the following exemplary ways: (i) Hard hand-off: Once the handing over criteria are fulfilled by the releasing PERS unit, the person's tracking is moved from the releasing PERS unit which stops the tracking to the receiving PERS unit that starts tracking (break before make); (ii) Soft Hand-off: Once the handing over criteria are fulfilled by the releasing PERS unit, the person's tracking is moved from the releasing PERS unit that keeps tracking the person and sends the information to the receiving PERS unit that starts tracking the person. The realizing PERS unit stops tracking when the receiving PERS acknowledges that it successfully tracks the person (make before break); and (iii) Co-tracking: Each PERS sub-system that sufficiently identifies the person performs the tracking as long as the received scatter signal doesn't decrease below a predefine threshold from the maximum received signal among all the active PERS units. In this mode, the system decision is based on majority based voting between all the PERS units.

Multiple Features Extraction

The "cleaned" echo signal vectors are used as the raw data for the features extraction unit. This unit extracts the features that mostly describe the instantaneous state of the monitored person. The following are examples for the set of the extracted features and the method it's extracted: Position—the position is extracted as the position (in case of 2D—angle/range, in case of 3D—x,y,z coordinates) metrics output of each array baseline. The actual person position at home will be determined as a "finger print" method, i.e., the most proximity to the pre-trained home position matrices (centroids) codebook. Posture—the person posture (sitting, standing, and laying) will be extracted by creating the person "image" by using, e.g., a back-projection algorithm. Both position and posture are extracted, for example, by operating, e.g., the Back-projection algorithm on received echo signals—as acquired from the multiple antennas array in SAR operational mode.

The following is the used procedure to find the human position and posture: Dividing the surveillance space into voxels (small cubic) in cross range, down range and height; Estimating the reflected EM signal from a specific voxel by the back projection algorithm; Estimating the human position by averaging the coordinates of the human reflecting voxels for each baseline (Synthetic Aperture Antenna Array); Triangulating all baselines' position to generate the human position in the environment; Estimating the human posture by mapping the human related high-power voxels into the form-factor vector; and Tracking the human movements in the environment (bedroom, restroom, etc.)

Human motion—The monitored human body may create vibrations and other motions (such as gestures and gait). Therefore, it introduces frequency modulation on the returned echo signal. The modulation due to these motions is referred to as micro-Doppler (m-D) phenomena. The human body's motion feature may be extracted by estimating the micro-Doppler frequency shift vector at the target distance from the system (down range). The following description and FIGS. 3A-3N elaborate on the aspect of human motion features extraction.

It is noted that the term "motion" refers to the motion of the body and/or of body parts without displacement of the whole body as a bulk, such as gestures, limb motions, posture changes such as sitting down or standing up, gait (separated from the displacement), motion suddenness (e.g., possible fall or collapse), etc. The term "movement" refers to the displacement of a person's body as a whole, irrespective of the motion of body parts such as the limbs (in case of movement detection by backpropagation algorithms, the movement may comprise only the radial components of displacement).

Non-wearable monitoring system 100 may comprise ultra-wide band (UWB) radio frequency (RF) interferometer 120 configured to transmit UWB RF signals at, and to receive echo signals from, an environment including at least one human, processing unit 225 configured to processing derive, e.g., at a slow signal derivation module 226, a range-bin-based slow signal from the received echo signals, the slow signal being spatio-temporally characterized over a plurality of spatial range bins and a plurality of temporal sub-frames, respectively, and feature extractor 240 configured to derive from the slow signal a Doppler signature and a range-time energy signature as motion characteristics of the at least one human.

The Doppler signature may be derived by comparing spectral signatures of sub-frames in the slow signals, which are related to identify human-related range bins and sub-frames. The energy signature may derived by evaluating powers of the slow signal at identified human-related range bins and sub-frames. The Doppler signature and/or the energy signature may be derived with respect to different body parts of the at least one human.

Feature extractor 240 may be further configured to derive location data to yield movement characteristics of the at least one human. The location data may be derived by detecting displacements of the at least one human using back-projection and/or by identifying human-related range bins and sub-frames in the slow signal. The derivation of the location data may be carried out using a spatio-temporal histogram of the range-time energy signature, by identifying on the histogram range changes of at least body parts of the at least one human.

System 100 may further comprise human state classifier 250 configured to classify the motion and movement characteristics of the at least one human to indicate a state of the at least one human, and abnormality situation pattern recognition module 262, e.g., as part of cognitive situation analysis module 260 configured to generate an alert once the indicated state is related to at least one specified emergency. The classification may carried out by identification of a most probable fit of one of a plurality of predefined states to the motion and movement characteristics and wherein the alert generation is based on pattern recognition with respect to previously indicated states.

Figure 3A:
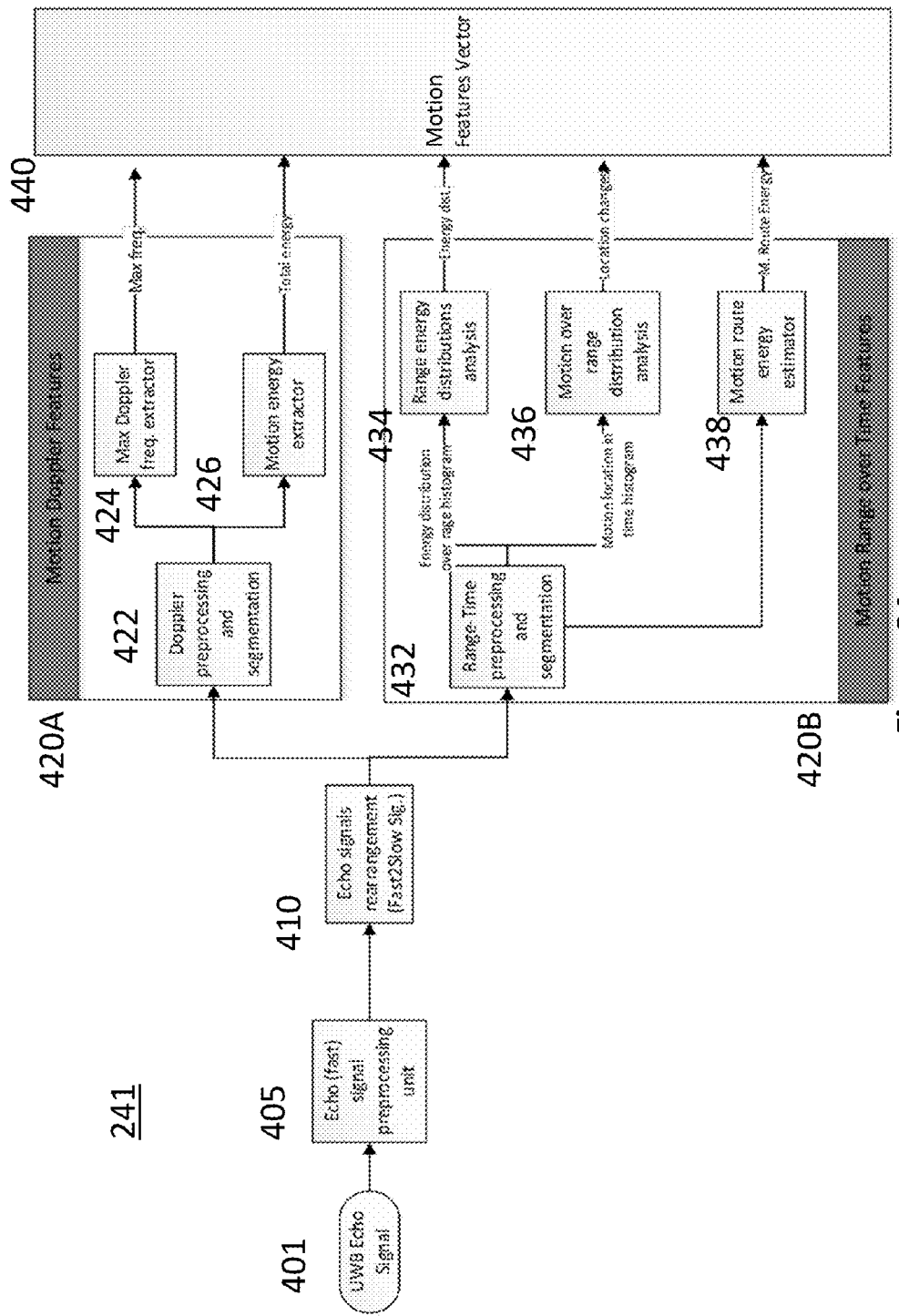
FIG. 3A is a high-level schematic flowchart illustration of exemplary motion feature extraction in feature extractor, according to some embodiments.

FIG. 3A is a high-level schematic flowchart illustration of exemplary human motion features extraction 241 in feature extractor 240, according to some embodiments. The Human Motion Features Extractor system receives a UWB echo signal 401 and processes it according to the following blocks. Detailed descriptions of modules in FIG. 3A are presented in consecutive figures.

Echo (fast) signal preprocessing unit 405 receives the echo signals from antennas 110-1 to 110-N. Each pulse transmission is represented by a vector that is referred to in the following as the 'fast time signal'. The transmission-reception cycle is performed repeatedly for a frame of, e.g., $T_{frame}=2$ to 5 seconds at a rate of, e.g., $F_{slow}=100$ Hz to 300 Hz as non-limiting values. The output of unit 405 is a matrix of the received echo signals, where each row is a fast time signal of a different transmission.

Figure 3B:
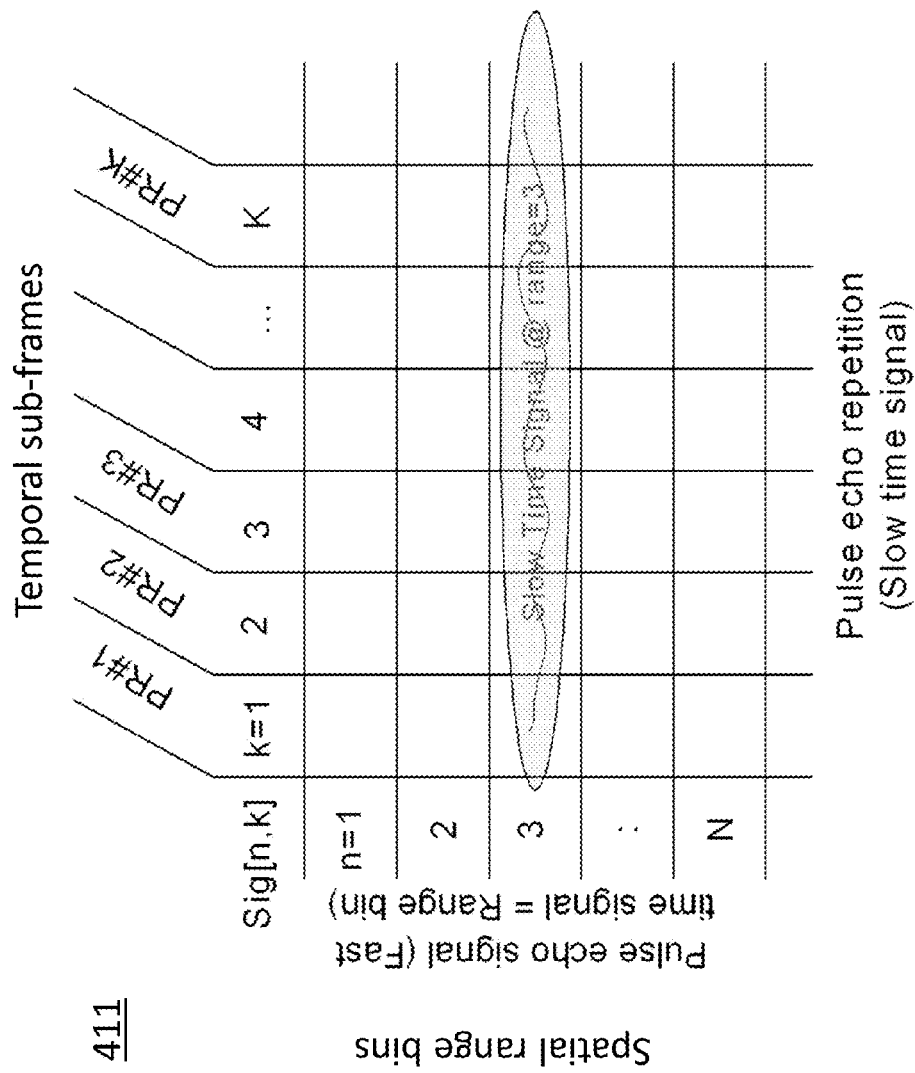
FIG. 3B is a high-level schematic illustration of fast and slow signal mapping, according to some embodiments.

Range bin based slow signal constructor (Fast2Slow) 410 rearranges the downrange echo (fast) signals vectors (the matrix rows) to represent the cross-range (slow) signals 411 (the matrix columns), as illustrated in FIG. 3B below. The slow signal vector represents a single downrange distance (bin) with a sampling rate, e.g., $F_{slow}=100$ Hz to 300 Hz as a non-limiting value. These vectors are referred as the 'slow time signals'.

Human body (target) detection is carried out by detecting its representation by a range bins window of, e.g., $RW_{target}=50$ to 200 range bins (assuming, in a non-limiting manner, that each range bin is approximately 1 cm), in a non-limiting example. The target location may be determined by the range bins window with the highest motion power among all of the $RW_{target}$ bins windows. The slow signal may be preprocessed for each range bin separately and may include DC removal, which is done by the subtraction of the estimated average DC signal from the original signal as well as other optional signal adjustments for example gain and phase mismatch correction between all the range bins slow signals and out-of-band noise reduction filtering.

Feature extraction 241 may be separated into two components—motion Doppler characteristics derivation 420A (motion Doppler features) and motion change over range bins and time characteristics derivation 420B (motion energy features). Motion features extraction 241 yields a motion features vector 440 which is then used for further processing and classification in classifiers 130 and/or 250. The following demonstrates in a non-limiting manner possible embodiments of derivations 420A, 420B.

Motion characteristics detection 420 may comprise deriving from the slow signal a Doppler signature, e.g., by block 420A, and a range-time energy signature, e.g., by block 420B, as motion characteristics of the at least one human.

Motion characteristics detection 420 may comprise, concerning derivation of Doppler signature 420A, Doppler preprocessing and segmentation 422 in which the slow signal frame is divided into $M_{subframes}$ sub-frames using Equation 6 (see below). The spectrogram may be generated by fast Fourier transform (FFT) for each slow time signal sub-frame within the human target range. A maximal Doppler frequency extractor 424 may use the maximum Doppler frequency to identify the instantaneous moment and range that a rapid motion (such as falling) has occurred. This feature is extracted by scanning all the slow time signal sub-frames per each range bin and accumulating the related power spectrum with the highest motion (Doppler) frequency that is selected out of each range bin. The maximal Doppler feature is extracted from the accumulated range bins power spectrums. A Motion Energy Extractor 426 may estimate the motion energy features in the frequency domain. There are a few features that are extracted to better represent the overall motion energy.

Motion characteristics detection 420 may comprise, concerning derivation of energy signature 420B, Range over Time preprocessing and segmentation 432 in which the signal is preprocessed and segmentation of the data into histograms is performed. For example, at a first stage, a Dynamic Time Wrapping (DTW) process may be implemented to estimate the human motion path along the range bins window and at a second stage, e.g., three histograms, which contain information about the distribution of the motion activity and energy signature over range, are generated to represent: (i) Cumulated energy of all the range bins selected; (ii) The numbers of appearances of each range bin in the top 5 range bins; and (iii) The number of average energy for each range bin that appeared in the top 5 ranges bins list. For each histogram, a set of features may be extracted to represent the histogram form factor, for example: (i) Motion energy distribution analysis 434 which comprises the extraction of features that represent the distribution of the energy over the range bins, carried out e.g. by using the energy distribution histogram analysis over range bins; (ii) Motion over range distribution analysis 436 to represent the distribution of the active range bins during the motion period and helps determine if the motion is stationary in space or distributed among several range bins; and (iii) Motion route energy estimator 438 which extracts the motion route energy by accumulating the power over the motion path (the selected range bins power as a result of the DTW at the pre-processing unit).

FIG. 3B is a high-level schematic illustration of fast and slow signal mapping 410, 411, according to some embodiments. The received preprocessed fast signals are mapped in a two dimensional matrix X (Equation 1). Each echo sample is an element on the matrix [n][k]; n=1 . . . $N_{Ranges}$; k=1 . . . $K_{Samples}$, where n is the downrange bin indicator of spatial range bin, and k is the cross-range (slow) time indicator of temporal bins. The number of total range bins is determined by the scanning window, while each range bin represents $C/F_{fast}$ meters ($F_{fast}$ is the echo signal sampling rate). The matrix is separated into its rows. Each row $x_n$ is the echo signal from the same range from the interferometer (radar), sampled in $F_{slow}$=250 Hz. Those vectors are referred as the slow time signals.

$$X(x[n][k]) = \begin{bmatrix} x[1][1] & \cdots & x[1][K] \\ \vdots & \ddots & \vdots \\ x[N][1] & \cdots & x[N][K] \end{bmatrix}$$ (Equation 1)

FIG. 3C is a high-level schematic flowchart illustration of exemplary human body target detection 452, according to some embodiments. Human Body Target Detection unit 452 narrows the focus of the analysis to the relevant range bins with human presence. Unit 452 may operate with various inputs, according to the required features to be extracted. The process of the target detection given the slow time signals of all the N range bins is performed by the following blocks, as an exemplary embodiment. A range bin power calculator 452A calculates the power of each slow time vector by Equation 2, where k and n are the time and range bin indicators respectively, to yield N power values.

$$p[n] = \Sigma_{k=1}^{K} x_n^2[k] \text{ for } n=1 \ldots N_{Ranges}$$ (Equation 2)

Following, the power sequence over a sliding window of $RW_{target}$ range bins is calculated along the ($N_{Ranges}$−$RW_{target}$+1) windows (Eq. 2.2) and accumulated by accumulator 452B.

$$s[n] = \Sigma_{j=0}^{M-1} p[j\text{'}n] \text{ for } n=1 \ldots (N_{Ranges} - RW_{target}+1)$$ (Equation 3)

Finally, the human target location region is detected 452C and indicated at the most powerful windowed power as expressed in Equation 4.

$$W\text{indicator} = \text{argmax}_n(s[n])$$ (Equation 4)

FIG. 3D is a high-level schematic flowchart illustration of an exemplary slow signal preprocessing unit 454, according to some embodiments. The slow time signal preprocessing may be carried out in a generic unit having its input determined by the extracted features (e.g., of features vector 440) and optionally operating on each slow time signal separately. Preprocessing unit 454 may perform the following blocks: (i) Adaptive DC removal 454A by continuously calculating the estimated DC signal (time varying DC) for each time bin by Equation 5, using the current slow signal vector x[k], $$s[k] = (1-a)s[k-1] + ax[k], k=1 \ldots K_{samples}$$ (Equation 5)

where a, is the learning coefficient. The estimated DC signal is subtracted from the original signal, namely y[k]=x[k]−s[k]. Gain mismatch correction 454B may optionally be performed to the selected range bins' slow signals to compensate the path losses differences among the selected range bins. The additional path loss of $R_i$ versus $R_{min}$ may be calculated as $$\Delta P.L.[dB] = 20\log\left(\frac{R_i}{R_{min}}\right),$$

where $R_i$ is the range bin i distance out of the selected set of range bins and $R_{min}$ is the first (closest) range bin. A slow signal phase mismatch correction 454C among the selected range bins may be carried out to compensate for the motion offset over the time/range bin. That is, the same motion profile may be preserved between neighbor range bins with a delayed version. The slow signal phase mismatch correction may estimate the phase error between $SlowSig_{Ri}$ and $SlowSig_{Rref}$, where $SlowSig_{Ri}$ is the slow signal of range bin $R_i$, and $SlowSig_{Rref}$ is the slow signal that is considered the reference range bin out of the selected range bins. Optionally, an out of band (O.O.B.) noise reduction filter 454D may be enabled to filter out the irrelevant slow signal components or interferences that might influence the performance of the various energy based features extraction.

Figure 3E:
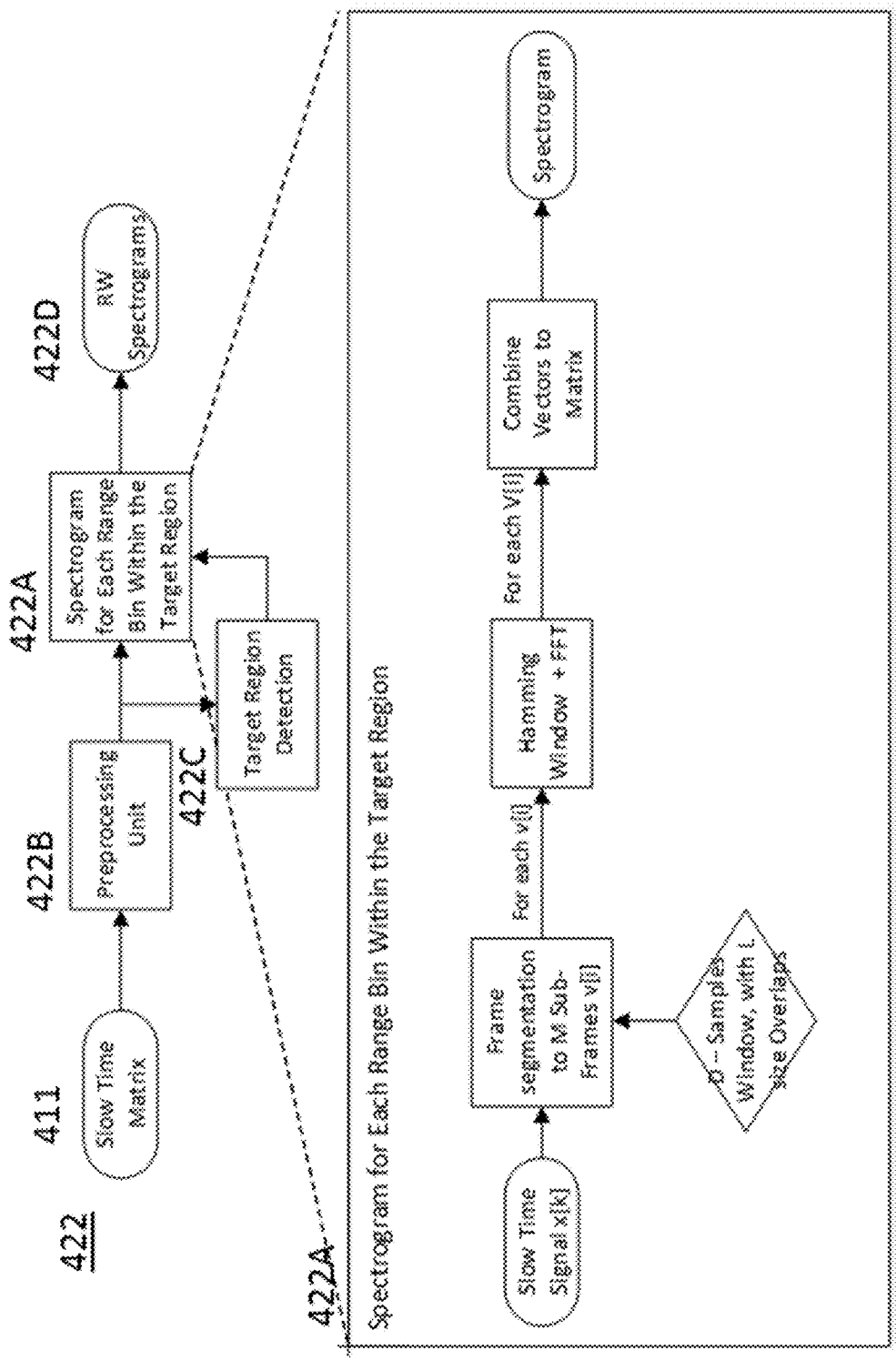
FIG. 3E is a high-level schematic flowchart illustration of exemplary Doppler preprocessing and segmentation, according to some embodiments.

FIG. 3E is a high-level schematic flowchart illustration of exemplary Doppler preprocessing and segmentation 422, according to some embodiments. A spectrogram 422A for each range bin may be generated and used for extraction of signal's spectral features, for every short time period, termed herein sub-frame (e.g., a plurality of specific fast signal times, i.e., a range of k values). The sub-frame period should be short enough to consider the motion as stationary). In order for a spectrogram to be created from a slow time signal vector of a specific range bin in the target region, slow time signal 411 of each range bin is first preprocessed by a preprocessing unit 422B, and then a human motion target detection unit 422C is being used to find the target range bin. Spectrogram 422A of each range bin is generated by segmenting the original signal x[k] to $M_{subframes}$ sub-vectors. For a given window size and number of overlaps, a new vectors group is constructed according to Equation 6.

$$\{v_m[i]\} = \{x[L_{step}m+i]\}; i=1 \ldots D; m=1 \ldots M_{subframe}$$ (Equation 6)

Each vector may have, as a non-limiting example, $D_{WinSize}$ may be between 50 and 200 samples (equivalent a subframe length of between 0.15 and 2 seconds) with overlaps of ($D_{WinSize}$−$L_{step}$) samples from the previous vector in the sequence ($L_{step}$=is the samples step size between subframes). Then, a power spectrum $V_m$ may be computed for each sub-frame by Equation 7, where h is a hamming window with length D.

$$\{V_m\} = FFT\{v_m \cdot h\}; m=1 \ldots M_{subframes}$$ (Equation 7)

This process is repeated for every range bin within the target region. $RW_{target}$ spectrograms 422D are gathered for further processing.

Figure 3F:
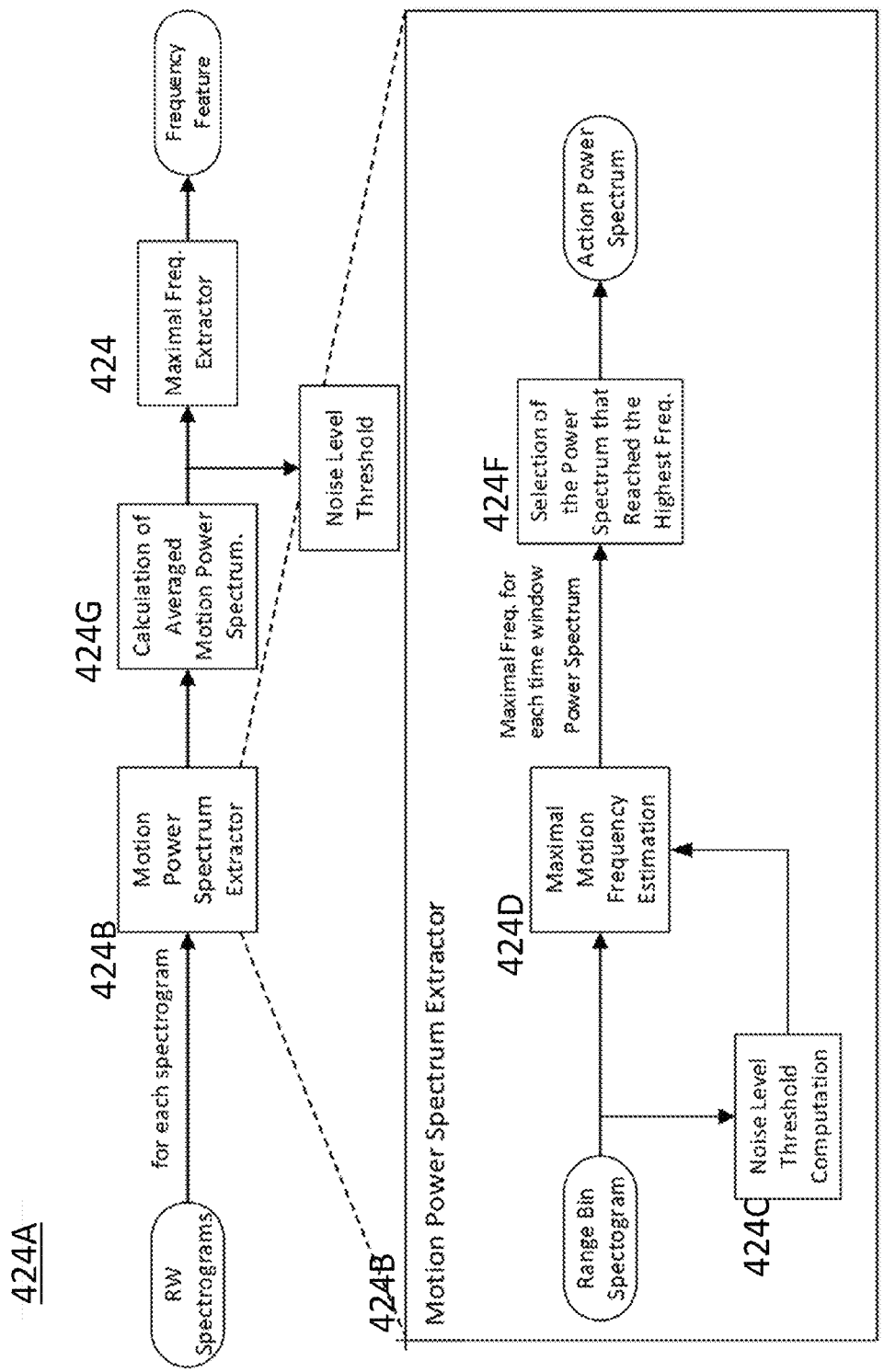
FIG. 3F is a high-level schematic flowchart illustration of an exemplary maximal Doppler frequency extraction, according to some embodiments.

FIG. 3F is a high-level schematic flowchart illustration of an exemplary maximal Doppler frequency extraction 424A, according to some embodiments. Maximal Doppler frequency extractor 424 is configured to find the highest velocity of the motion, which is represented by the motion's Doppler frequency along the motion's down-range route. The timing of the human peak motion activity is not common for all range bins, due to the fact that the motions can cross range bins versus the time. Therefore, the maximal Doppler frequency feature is extracted by scanning all the slow time signal sub-frames per each range bin and accumulating the related power spectrum with the highest motion (Doppler) frequency that is selected out of each range bin. The max Doppler feature may be extracted from the accumulated range bins power spectrums. In order to extract the action power spectrum by extractor 424B from each range bin spectrogram, the following process is performed: Noise level threshold estimation computation 424C calculates the noise level threshold for the spectrogram energy by considering the spectrogram values below noise level are considered as not related to human motion. A threshold $T_1$ (measured in dB) may be determined by Equation 8, using the mean of the upper four frequency bins of the spectrogram, while Q, P are respectively the numbers of frequency and time bins of the spectrogram matrix S.

$$T_1 = \frac{1}{4} \sum_{q=(Q-4)}^{q=Q} \frac{1}{P} \sum_{p=1}^{p=P} s[p,q], s \in S \quad \text{(Equation 8)}$$

The maximal motion frequency bin is defined and estimated in 424D, as the first frequency bin to its power below the motion threshold when scanning the spectrum from $F_{min}$ to $F_{max}$ which is the motion (active) region for the p power spectrum as defined by Equation 9.

$$f_p = \mathrm{argmin}_q(s[q,p] < (T_1+1)) \text{ for } p=1 \ldots P \quad \text{(Equation 9)}$$

where $f_p$ is the maximal frequency at the p power spectrum that its power is $<T_1+1$ dB. An example for that region from a full spectrogram can be seen in spectrogram 424E of FIG. 3G.

Figure 3G:
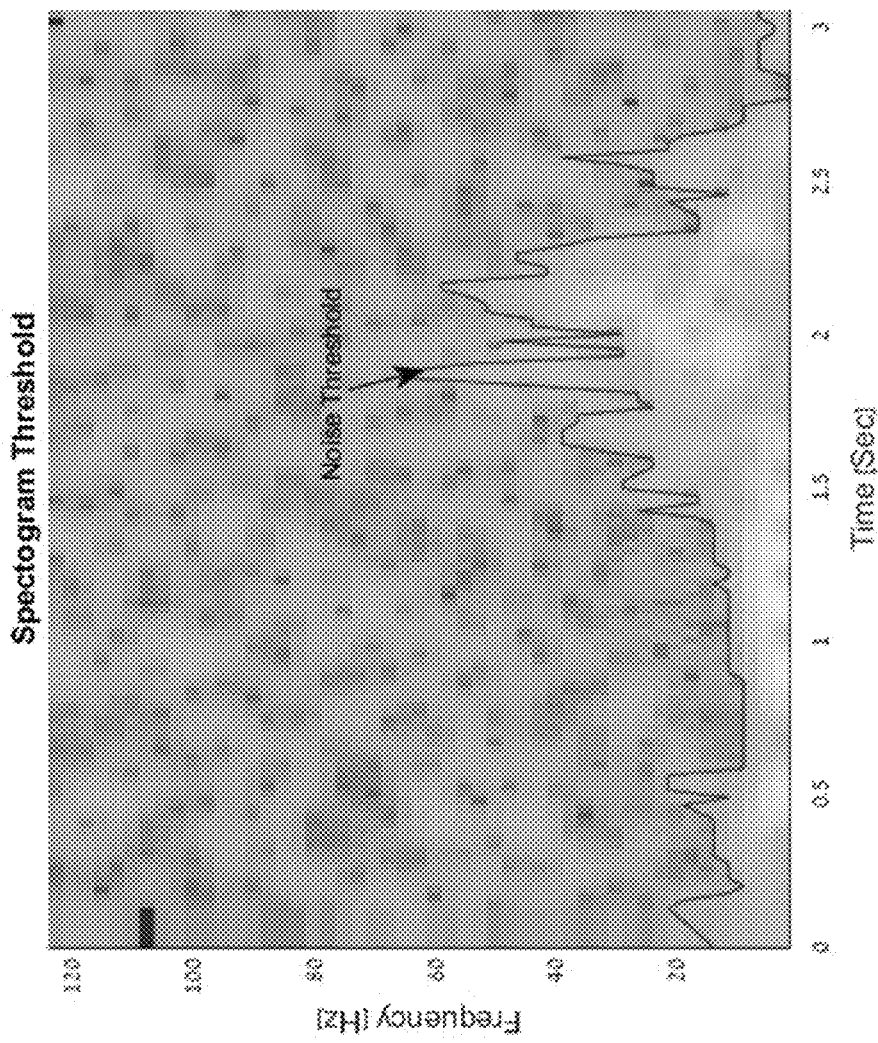
FIG. 3G is an exemplary illustration of a spectrogram of motion over a single range bin in the active area, according to some embodiments.

FIG. 3G is an exemplary illustration of a spectrogram 424E of motion over a single range bin in the active area, according to some embodiments. Action power spectrum extractor 424B further carries out a selection 424F of the power spectrum with the highest frequency—the selected power spectrum at time bin p is the one that has the highest value of $f_p$ (referred as action power spectrum of range q). This power spectrum is extracted for farther analysis. The averaged action power spectrum $P_{av}$ is created (424G) using action power spectrums 424E from all range bins. Then, a new noise threshold $T_2$ is calculated from Equation 10, by using the average value of the upper four frequency bins of the averaged (accumulated) power spectrums, in a non-limiting example.

$$T_2 = \frac{1}{4} \sum_{q=(Q-4)}^{q=Q} P_{av}[q] \quad \text{(Equation 10)}$$

The maximal frequency feature is calculated by Equation 11:

$$f_{max} = \mathrm{argmin}_q(P_{av}[q] < (T_2+1)) \quad \text{(Equation 11)}$$

Figure 3H:
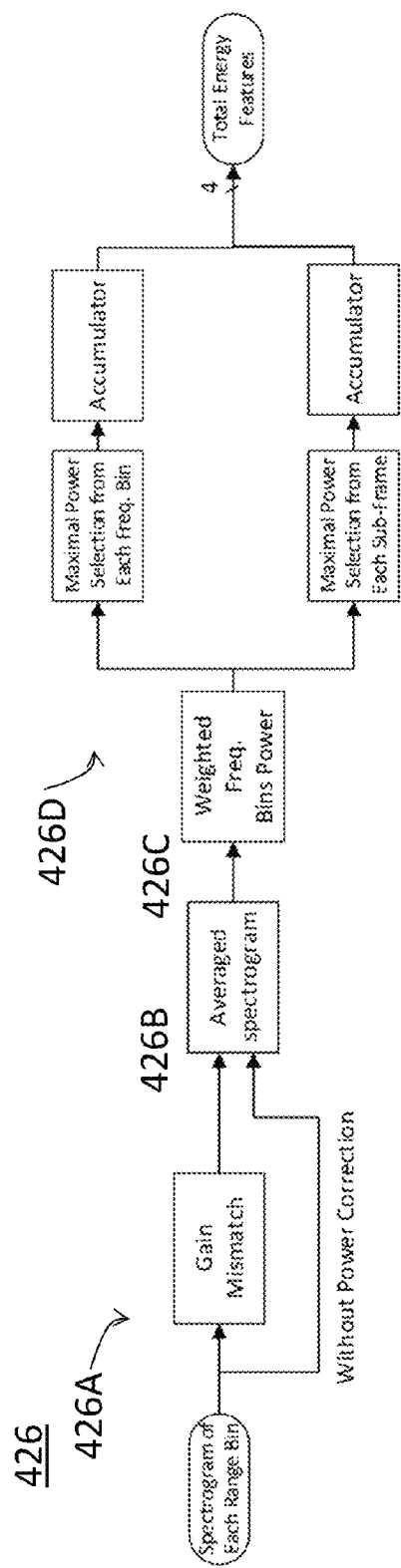
FIG. 3H is a high-level schematic flowchart illustration of an exemplary motion energy features extractor, according to some embodiments.

FIG. 3H is a high-level schematic flowchart illustration of an exemplary motion energy features extractor 426, according to some embodiments. The motion energy features may be estimated in the frequency domain. There are a few features that are extracted to better represent the overall motion energy. The motion energy might be affected by several conditions which are not related to the motion itself. For example, the relative distance from the interferometer as well as the motion duration. Unit 426 may create several spectrograms for all the target range bins to extract the various features that represent the energy signature. The motion energy features may be extracted by the following exemplary process. Two spectrogram versions may be created for each target range bin. The first spectrogram may be created after a range gain mismatch correction (to compensate the path loss variations over the range bins). The other spectrogram may be created without the gain mismatch correction (426A). The gain mismatch may be implemented at preprocessing unit 422B. Therefore, two spectrogram sets are created for the complete range bins $\{S_{1n}\}$ and $\{S_{2n}\}$. For each set of spectrograms, an average spectrogram 426B $S_{1av}$ $S_{2av}$ may be created by Equation 12.

$$S_{i,av}[q][m] = \frac{1}{RW} \sum_{n=1}^{RW} S_n[q][m]; \quad \text{(Equation 12)}$$

for $i = 1, 2$  $m = 1 \ldots M_{subframes}$, $q = 1 \ldots Q_{freqbins}$

In order to emphasize the motion power in higher frequencies, each averaged spectrogram frequency bin $\vec{S}_{av}^q$ may be processed with a corresponding weight, into a new weight-averaged spectrogram 426C by Equation 13.

$$\vec{SW}_{av}^q = \vec{S}_{av}^q * \sqrt{\frac{f[q]}{f_{max}}}; \text{ for } q = 1 \ldots Q_{freqbins} \quad \text{(Equation 13)}$$

where f[q] is the frequency value of the q frequency bin, and $f_{max}$ is the maximal frequency bin value. Two vectors of the power peaks may be created (426D) for each the two spectrograms, with and without power correction. A first vector $\vec{p}_1$ contains the maximal power of each sub-frame vector $\vec{s}_{av}^m$ (Equation 14A), and the second vector $\vec{p}_2$ contains the maximal values of each frequency bin vector $\vec{s}_{av}^q$ (Equation 14B).

$$p_1[m] = \max(\vec{s}_{av}^m); \text{ for } m=1 \ldots M_{subframes}(7.3) \quad \text{(Equation 14A)}$$

$$p_2[q] = \max(\vec{s}_{av}^q); f \text{ or } q=1 \ldots Q_{freqbins}(7.4) \quad \text{(Equation 14B)}$$

Each of the four (2×2) vectors—with the different procedures for gain processing and for maximal power values extraction, are accumulated into four energy features.

Figure 3I:
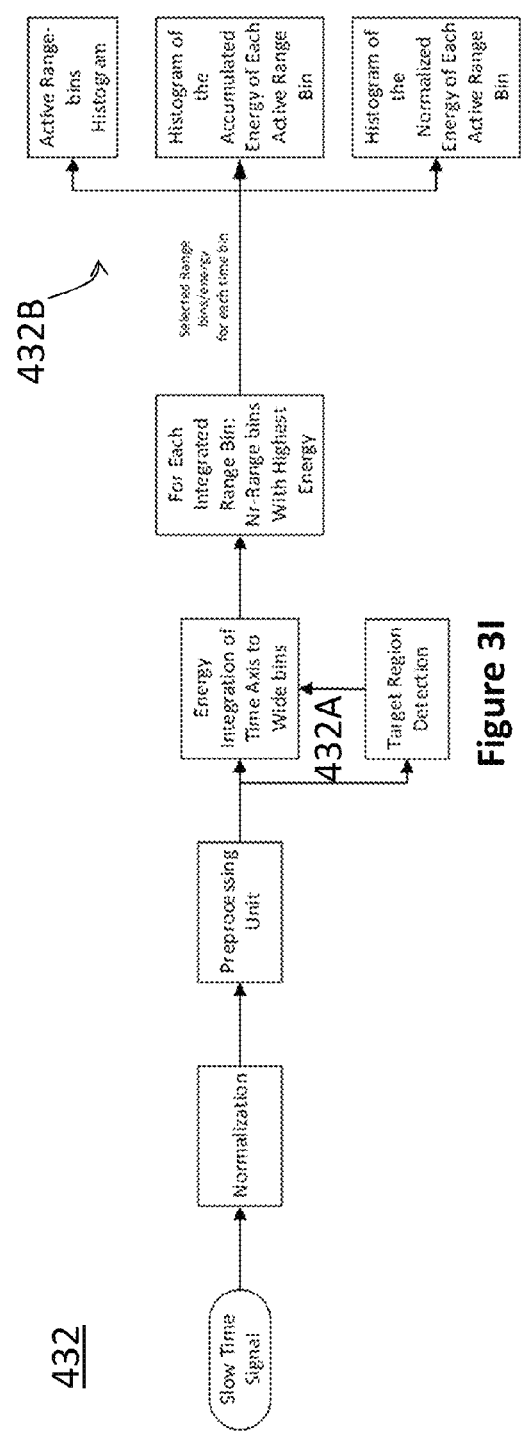
FIG. 3I is a high-level schematic flowchart illustration of an exemplary range-time preprocessing and segmentation flow as part of derivation of energy signature, according to some embodiments.

FIG. 3I is a high-level schematic flowchart illustration of an exemplary range-time preprocessing and segmentation flow 432 as part of derivation of energy signature 420B, according to some embodiments. The motion features over range-time helps profiling the energy signature of each motion, not only by characterizing its power and velocity, but by also characterizing its distribution over space along the motion time. Module 432 may be configured to create three histograms that express the distribution of motion energy and activity over the range bins during motion period. The energy related histograms may be created by the following algorithms. After normalization of the slow time matrix X (defined in Equation 1) using the highest absolute value amplitude as $$X = \frac{X}{\|X\|_\infty}$$

(the notation X is maintained for simplicity), the target region is located by a target region detector unit 432A. The two axis of the slow time matrix X correspond to the time of the sample (time bin) and the range of the sample (range bin). Each range bin vector, with $K_{Samples}=T_{frame} \cdot F_{slow}$ length as an example, may then segmented into 10 sub-frames as a non-limiting example and mapped in as new matrix $X_n$ defined in Equation 15, with $K_{samples}=800$ as a non-limiting example, with each row of the new matrix having $K_{samples}/10$ samples with an overlap.

$$X_n = \begin{bmatrix} x_n[1] & \cdots & x_n[80] \\ \vdots & \ddots & \vdots \\ x_n[720] & \cdots & x_n[800] \end{bmatrix} \quad \text{(Equation 15)}$$

With $E_n$ being the temporal energy vector of each range bin as calculated in Equation 16, j being the sub-frame number.

$$E_n[j] = \sum_{i=1}^{i=\frac{K}{10}} \|Xn[j, i]\|^2 \text{ for } n = 1 \ldots RW_{target} \quad \text{(Equation 16)}$$

A Matrix E defined by Equation 17 is constructed by gathering all the temporal energy vectors from each range bin.

$$E = \begin{bmatrix} E_1 \\ \vdots \\ E_N \end{bmatrix} \quad \text{(Equation 17)}$$

The columns of E are the energies of all the ranges along the new wider time bins, and the rows are the energy of a specific bin along time. From each column with indicator k, the five highest elements values may be extracted into $w_k(r)$, r=1 . . . 5; together with their row indexes $g_k(r)$, as a non-limiting example. The three histograms 432B are created from elements $w_k(r)$ as defined by Equations 18A-C. An accumulated range histogram with elements calculated by Equation 18A:

$$h_{acc}(n) = \sum_{k=1}^{k=K} w_k(r) * I_{(g_k(r)=n)} \text{ for } n=1 \ldots RW_{target} \quad \text{(Equation 18A)}$$

The indicator function $I_{(\omega \in \Omega)}$ is equal to 1 if the condition in the brackets is true.

An activity in range over time histogram, with elements calculated by Equation 18B:

$$h_{app}(n) = \sum_{k=1}^{k=K} I_{(g_k(r)=n)} \text{ for } n=1 \ldots RW_{target} \quad \text{(Equation 18B)}$$

A normalized energy histogram, with elements calculated by Equation 18C:

$$h_{norm}(n) = \begin{cases} \frac{h_{acc}(n)}{h_{app}(n)}, & h_{app}(n) > 0 \\ 0, & h_{app}(n) = 0 \end{cases} \text{ for } n = 1 \ldots RW_{target} \quad \text{(Equation 18C)}$$

Figure 3J:
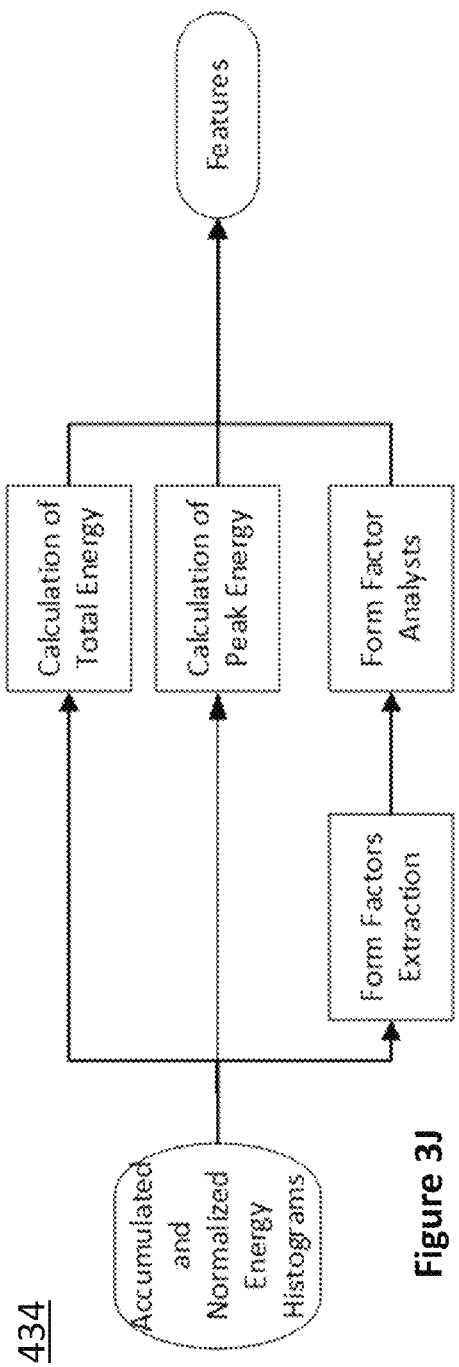
FIG. 3J is a high-level schematic flowchart illustration of an exemplary over-range energy distribution analysis as part of derivation of energy signature, according to some embodiments.

FIG. 3J is a high-level schematic flowchart illustration of an exemplary range energy distribution analysis 434 as part of derivation of energy signature 420B, according to some embodiments. Range energy distribution analysis module 434 extracts features from the accumulated and normalized energy histograms, which relate to the amount and distribution of motion energy over the range bins. Range energy distribution analysis 434 includes the extraction of the total and maximal (peak) energy over the range bins out of the histogram. In addition, the histogram form factor, defined as the percentage accumulated distribution points, is extracted (for example I20—identifies the range bin point that covers 20% of the accumulated motion energy, I40—identifies the range bin point that covers 40% of the accumulated motion energy, etc.).

Figure 3K:
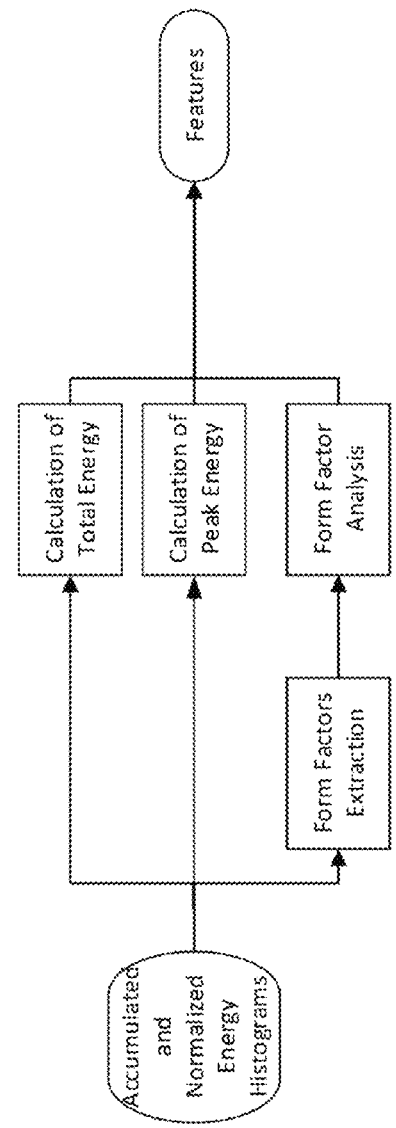
FIG. 3K is a high-level schematic flowchart illustration of an exemplary over-range activity distribution analysis, according to some embodiments.

FIG. 3K is a high-level schematic flowchart illustration of an exemplary motion over range distribution analysis 436, according to some embodiments. Motion over range distribution analysis unit 436 extracts features that relate to the distribution of active range bins over time, which is related to the motion's and varying over the down range. Unit 436 extracts the number of times that most of active region has been selected, the total number of active range bins and the mean number of repeated selection of the range bin as an active region.

Figure 3L:
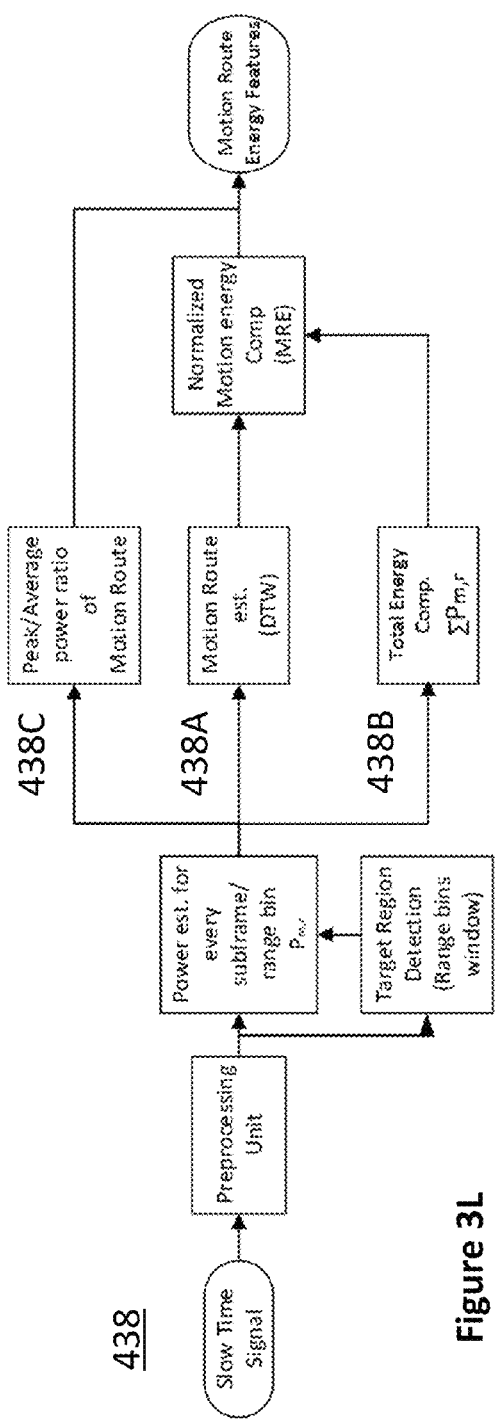
FIG. 3L is a high-level schematic flowchart illustration of an exemplary motion route energy estimation, according to some embodiments.
Figure 3M:
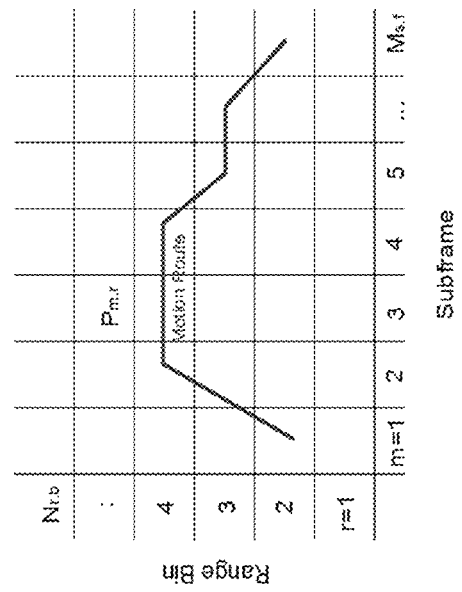
FIG. 3M, being a schematic matrix illustration of DTW-based motion route estimation, according to some embodiments.

FIG. 3L is a high-level schematic flowchart illustration of an exemplary motion route energy estimation 438, according to some embodiments. The motion route energy is defined as the accumulated power along the motion route in the range bins window during the motion period (time) relatively to the overall energy. This feature may be extracted in two major stages: (i) Estimating the motion route by using a dynamic Time Warping (DTW) approach 438A, (ii) accumulating the estimated power along the selected range bin route, and normalizing by the overall power 438B and calculating the motion route peak to average power ratio 438C. The DTW may be performed by selecting the highest range bin power for every sub-frame, as illustrated in FIG. 3M, being a schematic matrix illustration of DTW-based motion route estimation 438A, according to some embodiments. The relative Motion Route Energy (MRE) may be calculated as expressed in Equation 19:

$$MRE = \frac{\sum_{m=1}^{Msubframes} MP_{[m]}}{\sum_{m=1}^{Msubframes} \sum_{r=1}^{R} P_{[m,r]}} \quad \text{(Equation 19)}$$

Where:
$P_{[m,r]} = \sum_{n=1}^{N} |x_{m,r[n]}|^2$ is the power of subframe m, and Range bin r;

$x_{m,r[n]}$—is the Slow signal at subframe m and range bin r; and $MP[m] = \max\{P_{[m,r]}\}$, r∈Window Range bins, is the Max Power at subframe m.

The motion route Peak to Average Power Ratio (PAR), measured by the ratio between maximal and average power of the motion route, may be calculated as in Equation 20:

$$PAR = \frac{\max_m(MP[m])}{\frac{1}{Msubframes}\sum_{m=1}^{Msubframes} MP[m]} \quad \text{(Equation 20)}$$

Human breathing—During the breathing (respiration) the chest wall moves. The average respiratory rate of a healthy adult is usually 12-20 breaths/min at rest (~0.3 Hz) and 35-45 breaths/min (~0.75 Hz) during labored breathing. The breathing frequency feature is extracted by estimating the spectrum on the slow-time sampled received echo signal at the target distance (down range) from the system.

The features vector is prepared by quantizing the extracted features with a final number of bits per field and adding the time stamp for the prepared vector. This vector is used as the entry data for the human state classifier (for both training and classifying stages).

Figure 3N:
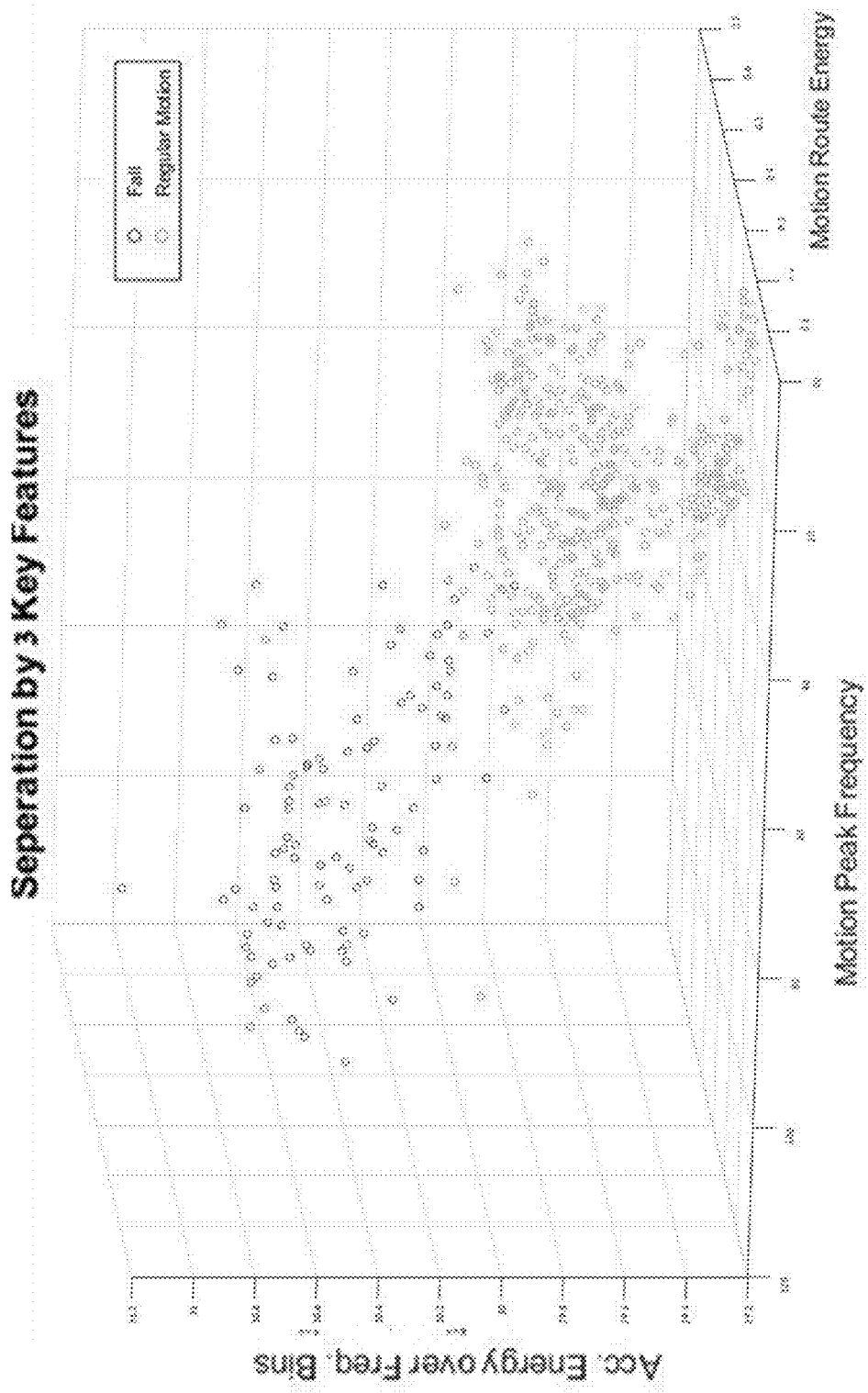
FIG. 3N is a schematic illustration of the possibility to separate different types of motions based on the derived parameters, according to some embodiments of the invention.

FIG. 3N is a schematic illustration of the possibility to separate different types of motions based on the derived parameters, according to some embodiments of the invention.

The two illustrations in FIG. 3N are of the same 3D graphics and are taken from different angles to illustrate the separation of the two types of motion in the 3D parameter space. FIG. 3N clearly illustrates the ability of the analysis described above to separate motions that are categorized, in the non-limiting illustrated case, as fall motions and as regular motions. The results may be used independently to detect falls, or be provided to the classifier for verification and augmentation with additional data and analysis results. Classification of the human state, as described in detail below, may relate to the derived motion characteristics as well as optionally to posture characteristics, respiration characteristics and position characteristics that may be derived from the received echo signals by implementing the disclosed methods, approaches and/or additional analysis of the received echo signals.

Human State Classifier

The Human state classifier is a VQ (Vector Quantization) based classifier. This classifier consists of two main phases: (i) Training phase—it's done offline (supervised training) and online (unsupervised training), where a stream of features vectors reflecting various states are used as a preliminary database for vector quantization and finding the set of code-vectors (centroids) that sufficiently representing the instantaneous human states. The set of the calculated code-vectors are called codebook. Some embodiments of the training sessions are provided in more details hereinafter. (ii) Classifying phase—it's executed during the online operation while an unknown features vector is entered into the classifier and the classifier determines what the most probable state that it represents. The classifier output is the determined states and the set of the measured statistical distances (probabilities), i.e., the probability of State-i given the observation-O (the features vector). The aforementioned probability scheme may be formulated by: P (Si|O). The determined instantaneous state is called "Local Decision". The VQ states are defined as the set of instantaneous states at various locations at the monitored home environment. Therefore, any state is a 2 dimension results which is mapped on the VQ state matrix. (iii) The State matrix consists of the state (row) and location (Column) followed by a time stamp. Typical elderly home environment consists of the specific locations (Primary zones) and others non-specified locations (Secondary zones). State is defined as the combination of posture/motion at a specific location (e.g. S21 will indicate sleeping at Bedroom).

FIG. 4 is a table 134 illustrating an exemplary states definition in accordance with some embodiments of the present invention. FIG. 5 is a table 135 illustrating an exemplary states matrix in accordance with some embodiments of the present invention.

Cognitive Situation Analysis (CSA)

The CSA's objective is to recognize the abnormal human patterns according to a trained model that contains the possible abnormal cases (e.g., fall). The core of the CSA, in this embodiment, may, in a non-limiting example a Hidden Markov Model (HMM) based pattern recognition. The CSA engine searches for states patterns that are tagged as an emergencies or abnormal patterns. These predefined patterns are stored in a patterns codebook. The output of the CSA is the Global recognized human situation.

FIG. 6 is a table 136 illustrating exemplary abnormal patterns in accordance with some embodiments of the present invention. It can be seen that in the first abnormal case (Critical fall), it appears that the person was sleeping in the leaving room (S25), then was standing (S45) and immediately fell down (S65). He stayed on floor (S15) and start being in stress due to high respiration rate (S75). The CSA may contain additional codebook (irrelevant codebook) to identify irrelevant patterns that might mislead the system decision.

Communication Unit

The communication unit creates the channel between the system and the remote caregiver (family member or operator center). It may be based on either wired (Ethernet) connectivity or wireless (e.g., cellular or WiFi communication or any other communication channel).

The communication unit provides the following functionalities: (i) This unit transmits any required ongoing situation of the monitored person and emergency alerts. (ii) It enables the two way voice/video communication with the monitored person when necessary. Such a communication is activated either automatically whenever the system recognizes an emergency situation or remotely by the caregiver. (iii) It enables the remote system upgrades for both software and updated codebooks (as will be in further detail below). (iv) It enables the communication to the centralized system (cloud) to share common information and for further big data analytics based on multiple deployments of such innovated system.

Figure 7:
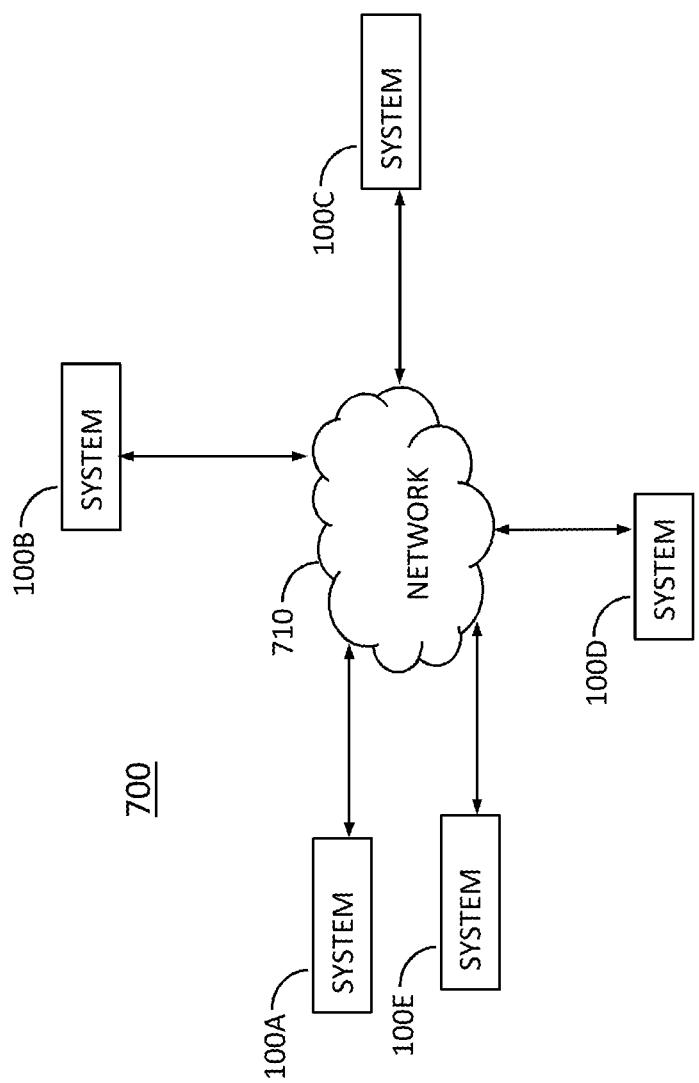
FIG. 7 is a diagram illustrating a cloud-based architecture of the system in accordance with some embodiments of the present invention.

FIG. 7 is a diagram illustrating cloud-based architecture 700 of the system in accordance with embodiments of the present invention. Raw data history (e.g., states stream) is passed from each local system 100A-100E to the central unit located on a cloud system 710 and performs various data analysis to find correlation of states patterns among the multiple users' data to identify new abnormal patterns that may be reflected just before the recognized abnormal pattern. New patterns code vectors will be included to the CSA codebook and cloud remotely updates the multiple local systems with the new code-book. The data will be used to analyze daily operation of local system 100A-100E.

Figure 8:
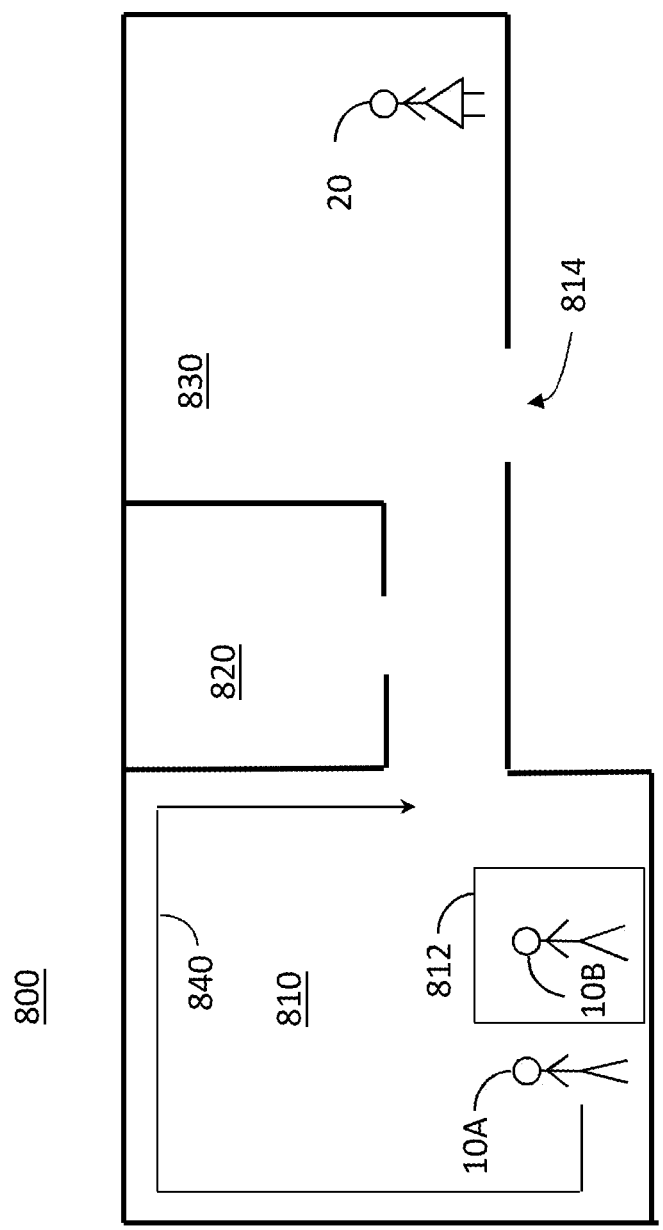
FIG. 8 is a floor plan diagram illustrating initial monitored person training as well as the home environment and primary locations training in accordance with embodiments of the present invention.

FIG. 8 is a diagram illustrating a floor plan 800 of an exemplary residential environment (e.g., an apartment) on which the process for the initial training is described herein. The home environment is mapped into the primary zones (the major home places that the monitored person attends most of the time as bedroom 810, restroom 820, living room 830 and the like) and secondary zones (the rest of the barely used environments). The VQ based human state classifier (described above) is trained to know the various primary places at the home. This is done during the system setup while the installer 10A (being the elderly person or another person) stands or walks at each primary place such as bedroom 810, restroom 820, and living room 830 and let the system learns the "fingerprint" of the echo signals extracted features that mostly represents that place. These finger prints are stored in the VQ positions codebook. In addition, the system learns the home external walls boundaries. This is done during the system setup while the installer stands at various places along the external walls and lets the system tune its power and processing again (integration) towards each direction. For example, in bedroom 810, installer 10A may walk along walls in route 840 so that the borders of bedroom 810 are detected by tracking the changes in the RF signal reflections throughout the process of walking. A similar border identification process can be carried out in restroom 820, and living room 830. Finally, the system learns to identify the monitored person 10B. This is done by capturing the fingerprint of the extracted features on several conditions, such as (1) while the person lays at the default bed 812 (where he or she is supposed to be during nighttime) to learn the overall body volume, (2) while the person is standing to learn the stature, and (3) while the person walks to learn the gait. All the captured cases are stored in the VQ unit and are used to weight the pre-trained codebooks and to generate the specific home/person codebooks. According to some embodiments, one or additional persons such as 20 can also be monitored simultaneously. The additional person can be another elderly person with specific fingerprint or it can be a care giver who needs not be monitored for abnormal postures.

Figure 9:
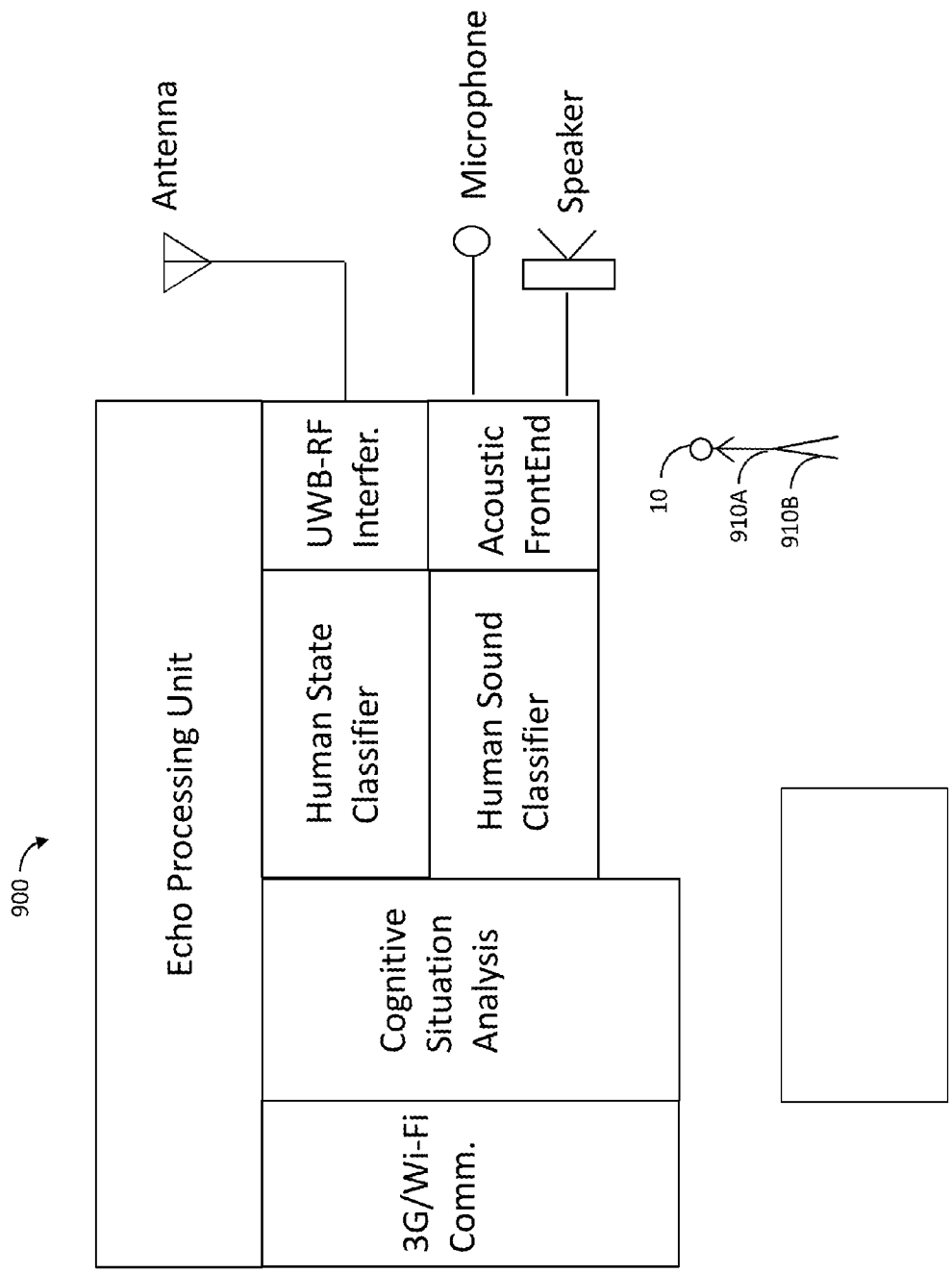
FIG. 9 is a diagram illustrating yet another aspect in accordance with some embodiments of the present invention.

FIG. 9 is a diagram illustrating yet another aspect in accordance with some embodiments of the present invention. System 900 is similar to the system described above but it is further enhanced by the ability to interface with at least one wearable medical sensor 910A or 910B coupled to the body of human 10 configured to sense vital signs of human 10, and a home safety sensor 920 configured to sense ambient conditions at said specified area, and wherein data from said at least one sensor are used by said decision function for improving the decision whether an abnormal physical event has occurred to the at least one human in said specified area. The vital signs sensor may sense ECG, heart rate, blood pressure, respiratory system parameters and the like. Home safety sensors may include temperature sensors, smoke detector, open door detectors and the like. Date from all or some of these additional sensors may be used in order to improve the decision making process described above.

Figure 10:
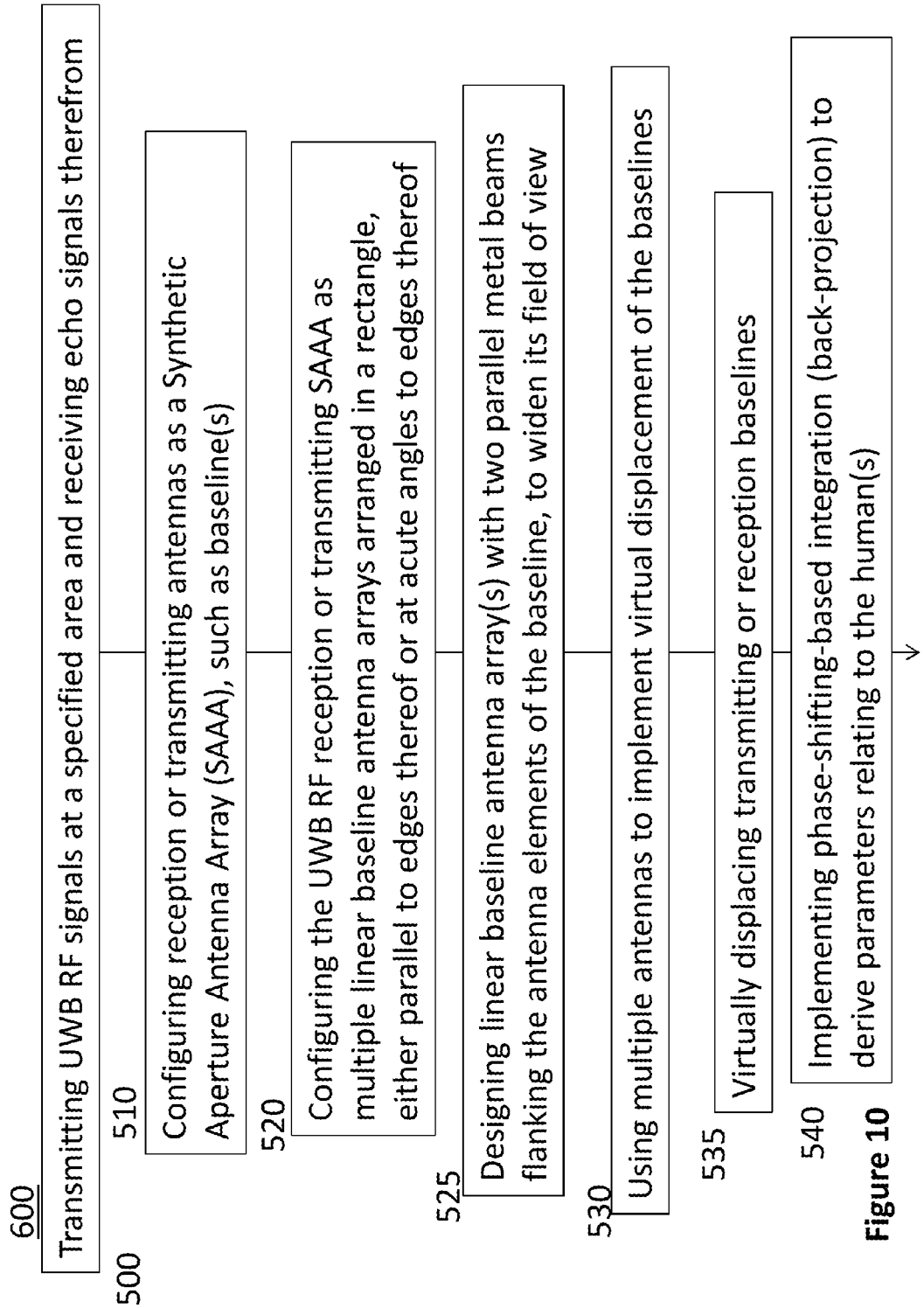
FIG. 10 is a high level schematic flowchart of a method, according to some embodiments of the invention.

FIG. 10 is a high level schematic flowchart of a method 600 according to some embodiments of the invention.

Method 600 may comprise transmitting UWB RF signals via transmitting antenna(s) at a specified area (such as an environment including at least one human) and receiving echo signals via reception antenna(s) (stage 500). At least one of the UWB RF transmitting and reception antennas comprises a Synthetic Aperture Antenna Array (SAAA) comprising a plurality of linear baseline antenna arrays ("baselines"). Method 600 may comprise configuring reception antenna(s) and/or transmitting antennas(s) as a Synthetic Aperture Antenna Array (SAAA), such as baseline(s) (stage 510), for example, method 600 may comprise configuring the UWB RF reception SAAA as a plurality of linear baseline antenna arrays arranged in a rectangle as a non-limiting example, possibly parallel to edges thereof or at acute angles to edges thereof (stage 520), e.g., as illustrated below in a non-limiting manner. Method 600 may comprise designing at least one of the linear baseline antenna arrays to comprise two (or more) parallel metal beams flanking the antenna elements of the baseline, to widen the baseline's field of view (stage 525).

Method 600 may further comprise using multiple antennas to implement virtual displacement of the baselines (stage 530), i.e., virtually displacing transmitting or reception baselines to enhance performance (stage 535). Method 600 may further comprise implementing phase-shifting-based integration (back-projection) to derive parameters relating to the human(s) (stage 540), such as location, movement and/or posture features.

Method 600 may further comprise canceling environmental clutter (stage 605), e.g., by filtering out static non-human related echo signals (stage 606), extracting from the filtered echo signals, a quantified representation of position postures, movements, motions and breathing of at least one human located within the specified area (stage 610), identifying a most probable fit of human current state that represents an actual human instantaneous status (stage 690) and applying a pattern recognition based decision function to the identified states patterns and determine whether an abnormal physical event has occurred to the at least one human in the specified area (stage 693) (see additional details below).

Method 600 may further comprise finding the best match to a codebook which represents the state being a set of human instantaneous condition/situation which is based on vector quantized extracted features (stage 691).

Method 600 may further comprise ensuring, by the filtering out, that no human body is at the environment, using static clutter estimation and static clutter subtraction (stage 607).

Method 600 may further comprise quantizing the known states features vectors and generating the states code-vectors (stage 692A), measuring the distance between unknown tested features vectors and pre-defined known code-vectors (stage 692B) and finding the best fit between unknown tested features vector and pre-determined code-vectors set, using the most probable state and the relative statistical distance to the tested features vector (stage 692C).

Method 600 may further comprise generating the set of abnormal states patterns as a reference codebook, a set of states transition probabilities, and a states-patterns matching function to find and alert on a match between a tested states pattern and the pre-defined abnormal pattern of the codebook (stage 694). Method 600 may further comprise communicating an alert upon determining of an abnormal physical event (stage 695).

Method 600 may further comprise estimating the reflected clutter from a specific voxel to extract the human position and posture features (stage 612A), extracting the human motions and breathing features using Doppler signatures (stage 612B) and creating a quantized vectors of the extracted features (stage 612C).

Method 600 may further comprise processing the received echo signals to yield a range-bin-based slow signal that is spatio-temporally characterized over a plurality of spatial range bins and a plurality of temporal sub-frames, respectively (stage 620) and deriving from the slow signal a Doppler signature and a range-time energy signature as motion characteristics of the at least one human (stage 630). Method 600 may comprise deriving the Doppler signature by comparing spectral signatures of sub-frames in the slow signals, which are related to identified human-related range bins and sub-frames (stage 622) and deriving the energy signature by evaluating powers of the slow signal at identified human-related range bins and sub-frames (stage 624). Method 600 may comprise deriving the Doppler signature and/or the energy signature with respect to different body parts of the at least one human (stage 626).

Deriving 630 may further comprise deriving location data as movement characteristics of the at least one human (stage 632). Deriving of the location data 632 may comprise detecting displacements of the at least one human using back-projection (stage 634), using the received echo signals to derive, by back projection, 2D location data and 3D posture data about the at least one human (stage 635), and/or identifying human-related range bins and sub-frames in the slow signals (stage 636). Deriving of the location data 632 may be carried out using a spatio-temporal histogram of the range-time energy signature and by identifying on the histogram range changes of at least body parts (e.g., limbs) of the at least one human (stage 638). The motion characteristics and/or movement characteristics may comprise gait parameters.

Method 600 may further comprise handing over detecting 634 among a plurality of interferometry units according to detected displacements (stage 640), i.e., using different interferometry units for detection 634 according to displacement parameters, such as coverage region, signal intensity etc., as explained below. Method 600 may be carried out by a plurality of UWB RF reception SAAAs positioned at a plurality of positions, and may further comprise integrating the received echo signals from the UWB RF reception SAAAs (stage 642).

Method 600 may comprise classifying the position and/or posture and/or motion and/or movement and/or respiration characteristics of the at least one human to indicate a state of the at least one human (stage 688). Classification 688, e.g., by identifying the most probable fit 690, may be carried out by identifying a most probable fit of one of a plurality of predefined states to the motion characteristics.

Communicating the alert 695 may be carried out by generating the alert once the indicated state is related at least one specified emergency. The alert generation may be based on pattern recognition with respect to previously indicated states.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. An ultra-wide band (UWB) radio frequency (RF) interferometry unit comprising:
   an UWB RF pulse generator configured to generate UWB RF pulses having specified pulse characteristics,
   at least one UWB RF transmitting antenna configured to receive the generated UWB RF pulses and transmit corresponding UWB RF signals at an environment including at least one human,
   at least one UWB RF reception antenna configured to receive echo signals from the environment,
   an UWB RF interferometer configured to deliver the received echo signals for processing, and
   an environmental clutter cancellation module configured to filter out static non-human related echo signals;
   wherein at least one of: the at least one UWB RF transmitting antenna and the at least one UWB RF reception antenna, comprises a Synthetic Aperture Antenna Array (SAAA),
   wherein the SAAA comprises a plurality of linear baseline antenna arrays ("baselines"), and
   wherein the processing of the delivered echo signals is carried out by (i) a human state classifier configured to identify a most probable fit of a human current state that represents an actual human instantaneous state, and to find a best match to a codebook which represents the current state as being a set of human instantaneous conditions/situations which is based on a quantized feature status; and by (ii) an abnormality situation pattern recognition module configured to apply a pattern recognition based decision function to an identified states patterns and determine whether an abnormal physical event has occurred to the at least one human in the specified area.

2. The UWB RF interferometry unit of claim 1, wherein at least one of the baselines comprises two parallel metal beams flanking the antenna elements of the baseline.

3. The UWB RF interferometry unit of claim 1, wherein the SAAA comprises at least four baselines arranged in parallel to edges of a rectangle.

4. The UWB RF interferometry unit of claim 3, wherein the baselines are tilted with respect to a common plane thereof.

5. The UWB RF interferometry unit of claim 1, wherein the baselines are arranged to cover 360° around the unit and have pairwise overlapping beams.

6. The UWB RF interferometry unit of claim 1, wherein the UWB RF interferometer is further configured to use multiple antennas to implement virtual displacement of the baselines.

7. The UWB RF interferometry unit of claim 6, wherein the multiple antennas are reception antennas and the virtual displaced baselines are transmitting baselines.

8. The UWB RF interferometry unit of claim 6, wherein the multiple antennas are transmitting antennas and the virtual displaced baselines are reception baselines.

9. A non-wearable monitoring system comprising the UWB RF interferometry unit of claim 1 and further comprising:
a human state feature extractor configured to extract from the filtered echo signals, a quantified representation of position postures, movements, motions and breathing of at least one human located within the specified area,
a human state classifier configured to identify a most probable fit of human current state that represents an actual human instantaneous status, and
an abnormality situation pattern recognition module configured to apply a pattern recognition based decision function to the identified states patterns and determine whether an abnormal physical event has occurred to the at least one human in the specified area.

10. The non-wearable monitoring system of claim 9, comprising a plurality of the UWB RF interferometry units, wherein the system is further configured to implement at least one hand-over algorithm among the interferometry units with respect to the received echo signals from the at least one human in the environment.

11. The non-wearable monitoring system of claim 9, comprising a plurality of communicating sub-units, each having the UWB RF interferometry unit, the human state feature extractor and the human state classifier, wherein the abnormality situation pattern recognition module is further configured to integrate input from all sub-units.

12. A method comprising:
transmitting ultra-wide band (UWB) radio frequency (RF) signals via at least one UWB RF transmitting antenna at an environment including at least one human and receiving echo signals therefrom via at least one UWB RF reception antenna, and
canceling environmental clutter by filtering out static non-human related echo signals,
wherein at least one of: the at least one UWB RF transmitting antenna and the at least one UWB RF reception antenna comprises a Synthetic Aperture Antenna Array (SAAA),
wherein the SAAA comprises a plurality of linear baseline antenna arrays ("baselines"), and
wherein the processing of the delivered echo signals is carried out by (i) a human state classifier configured to identify a most probable fit of a human current state that represents an actual human instantaneous state, and to find a best match to a codebook which represents the current state as being a set of human instantaneous conditions/situations which is based on a quantized feature status; and by (ii) an abnormality situation pattern recognition module configured to apply a pattern recognition based decision function to an identified states patterns and determine whether an abnormal physical event has occurred to the at least one human in the specified area.

13. The method of claim 12, further comprising arranging the baselines in a rectangle, either parallel to edges thereof or at acute angles to edges thereof.

14. The method of claim 12, further comprising using multiple antennas to implement virtual displacement of the baselines.

15. The method of claim 14, wherein the multiple antennas are reception antennas and the virtual displaced baselines are transmitting baselines or wherein the multiple antennas are transmitting antennas and the virtual displaced baselines are reception baselines.

16. The method of claim 12, further comprising implementing phase-shifting-based integration to derive parameters relating to the at least one human.

17. The method of claim 12, further comprising:
using the received echo signals to derive, by back projection, 2D location data and 3D posture data about the at least one human,
classifying the 2D location data and the 3D posture data to indicate a state of the at least one human, by identifying a most probable fit of one of a plurality of predefined states to the 2D location data and the 3D posture data, and
generating an alert once the indicated state is related at least one specified emergency, the alert generation based on pattern recognition with respect to previously indicated states.

* * * * *